(12) United States Patent
Van Der Spek et al.

(10) Patent No.: US 9,645,001 B2
(45) Date of Patent: May 9, 2017

(54) PERFORMANCE MONITORING OF INDIVIDUAL HYDROCYCLONES USING SONAR-BASED SLURRY FLOW MEASUREMENT

(75) Inventors: Alex M. Van Der Spek, Rotterdam (NL); Robert J. Maron, Middletown, CT (US); Paul Joseph Rothman, Windsor, CT (US); Christian V. O'Keefe, Durham, CT (US); Douglas H. Loose, Southington, CT (US)

(73) Assignee: CiDRA Corporate Services, Inc., Wallingford, CT (US)

( * ) Notice: Subject to any disclaimer, the term of this patent is extended or adjusted under 35 U.S.C. 154(b) by 732 days.

(21) Appl. No.: 13/389,546

(22) PCT Filed: Aug. 11, 2010

(86) PCT No.: PCT/US2010/045178
§ 371 (c)(1),
(2), (4) Date: Apr. 24, 2012

(87) PCT Pub. No.: WO2011/019823
PCT Pub. Date: Feb. 17, 2011

(65) Prior Publication Data
US 2012/0209550 A1      Aug. 16, 2012

Related U.S. Application Data

(60) Provisional application No. 61/232,875, filed on Aug. 11, 2009, provisional application No. 61/400,819, (Continued)

(51) Int. Cl.
*G04C 11/00*       (2006.01)
*G01F 1/708*       (2006.01)
(Continued)

(52) U.S. Cl.
CPC ............ *G01F 1/7082* (2013.01); *B04C 11/00* (2013.01); *G01N 15/02* (2013.01); *G01N 15/10* (2013.01);
(Continued)

(58) Field of Classification Search
CPC .... B04C 5/08; B04C 5/28; B04C 1/00; B04C 3/06; B04C 5/25; B04C 11/00;
(Continued)

(56) References Cited

U.S. PATENT DOCUMENTS 3,596,839 A    8/1971  Putnam
4,026,479 A    5/1977  Bradburn et al.
(Continued)

FOREIGN PATENT DOCUMENTS

WO         9107231       5/1991
WO       2009137828    11/2009

OTHER PUBLICATIONS

O'Keefe C. V., Maron R.M., Gajardo L., (2007), Application of passive sonar technology to minerals processing applications. MAPLA 2007.
(Continued)

*Primary Examiner* — Jonathan C Teixeira Moffat
*Assistant Examiner* — Lynda Dinh
(74) *Attorney, Agent, or Firm* — Ware, Fressola, Maguire & Barber LLP

(57) ABSTRACT

Apparatus features a signal processor module that responds to signals containing information about sensed sound propagating through a slurry flowing in part, including overflow pipes, of cyclones operating in parallel on a cyclone battery, and determine corresponding signaling containing information about the performance of individual cyclones based upon the signals received. The signal processor forms part of a non-invasive acoustic-based passive monitoring system
(Continued)

having cyclones and sensors attached thereto. The signal processor module provides the corresponding signaling as output or control signaling, e.g., for controlling the cyclone battery.

21 Claims, 22 Drawing Sheets

Related U.S. Application Data filed on Aug. 2, 2010, provisional application No. 61/370,154, filed on Aug. 3, 2010.

(51) Int. Cl.
| | |
|---|---|
| B04C 11/00 | (2006.01) |
| G01N 15/02 | (2006.01) |
| G01N 15/10 | (2006.01) |
| G01N 29/036 | (2006.01) |
| B04C 5/24 | (2006.01) |
| G01N 15/00 | (2006.01) |
| G01N 29/46 | (2006.01) |

(52) U.S. Cl.
CPC .............. *G01N 29/036* (2013.01); *B04C 5/24* (2013.01); *G01N 29/46* (2013.01); *G01N 2015/0053* (2013.01); *G01N 2015/1087* (2013.01); *G01N 2291/02416* (2013.01)

(58) Field of Classification Search
CPC ........... B03D 1/00; G01F 1/34; G01F 1/7082; B01D 21/26; B01D 21/262; B01D 21/265; B01D 21/267; B01D 36/00; G01N 15/02; G01N 15/10; G01N 2015/0053; G01N 2015/1087; G01N 29/036; G01N 29/46; G01N 2291/02416
USPC .......................................................... 702/63
See application file for complete search history.

(56) References Cited

U.S. PATENT DOCUMENTS

| | | | | |
|---|---|---|---|---|
| 4,246,576 | A * | 1/1981 | Grieve et al. ................. | 340/606 |
| 5,132,024 | A | 7/1992 | Hulbert | |
| 5,248,442 | A | 9/1993 | Hulbert | |
| 5,765,967 | A * | 6/1998 | Klaymar ....................... | 405/179 |
| 6,246,576 | B1 | 6/2001 | Sands et al. | |
| 7,134,320 | B2 | 11/2006 | Gysling et al. | |
| 7,165,464 | B2 | 1/2007 | Gysling et al. | |
| 7,343,820 | B2 | 3/2008 | Gysling et al. | |
| 7,363,800 | B2 | 4/2008 | Gysling | |
| 7,367,240 | B2 | 5/2008 | Gysling et al. | |
| 7,603,916 | B2 * | 10/2009 | Gysling ...................... | 73/861.42 |
| 7,623,976 | B2 * | 11/2009 | Gysling et al. .................. | 702/47 |
| 2004/0022128 | A1 | 2/2004 | Liljenberg et al. | |
| 2004/0182754 | A1 | 9/2004 | Lange | |
| 2004/0255695 | A1 | 12/2004 | Gysling et al. | |
| 2005/0011258 | A1 | 1/2005 | Gysling et al. | |
| 2005/0061060 | A1 | 3/2005 | Gysling et al. | |
| 2005/0103691 | A1 | 5/2005 | Hakola | |
| 2005/0150330 | A1 | 7/2005 | Rajic et al. | |
| 2005/0173354 | A1 | 8/2005 | Binot et al. | |
| 2006/0219603 | A1 | 10/2006 | Bourke | |
| 2008/0236298 | A1 | 10/2008 | Gysling | |
| 2010/0044287 | A1 * | 2/2010 | Blum ........................ | B04C 5/28 210/97 |

OTHER PUBLICATIONS

Viega et al., "Application of Passive Sonar Technology to Long Standing Measurement Challenges in Industrial Processes." Datasheet [online]. Cidra Corporation, Nov. 4, 2007 (Nov. 4, 2004) [Retrieved on Oct. 5, 2010], Retrieved from the Internet: <URL:http://www.cidra.com/document_library/BI0291_ISA_Calgary_2007_Final_04-11-07.pdf>. especially pp. 1, 4-6, 10, 12, 16, 20-22, 25.

Williams, "Low Cost Radar and Sonar using Open Source Hardware and Software." Thesis [online]. University of Capetown, Aug. 2008 (Aug. 2008) [Retrieved on Oct. 5, 2010], Retrieved from the Internet: <URL:http//rrsg.uct.ac.za/theses/msc_theses/lwilliams_thesis.pdf>.

O'Keefe et al.,\, "Description of Non-Intrusive Sonar Array-Based Technology and its Application to Unique and Difficult Slurry and Paste Flow Measurements." Datasheet [online]. Cidra Corporation, 2009 [Retrieved on Oct. 5, 2010]. Retrieved from the Internet:<URL:http://www.cidra.com/document_library/BI0339_Paste_2008_022508_final.pdf>.

Mineral Communition circuits, their operation and optimization. JKMRC Technology Transfer, 2 pgs. 1993.

O'Keefe C.V., Maron R.J., Rothman P.J., Poplawski J., Description of Non-Intrusive Sonar Array-Based Technology and its Application to Unique and Difficult Slurry and Paste Flow Measurements, Presented at Paste 2008, Kaskane, Botswana, May 2008.

* cited by examiner

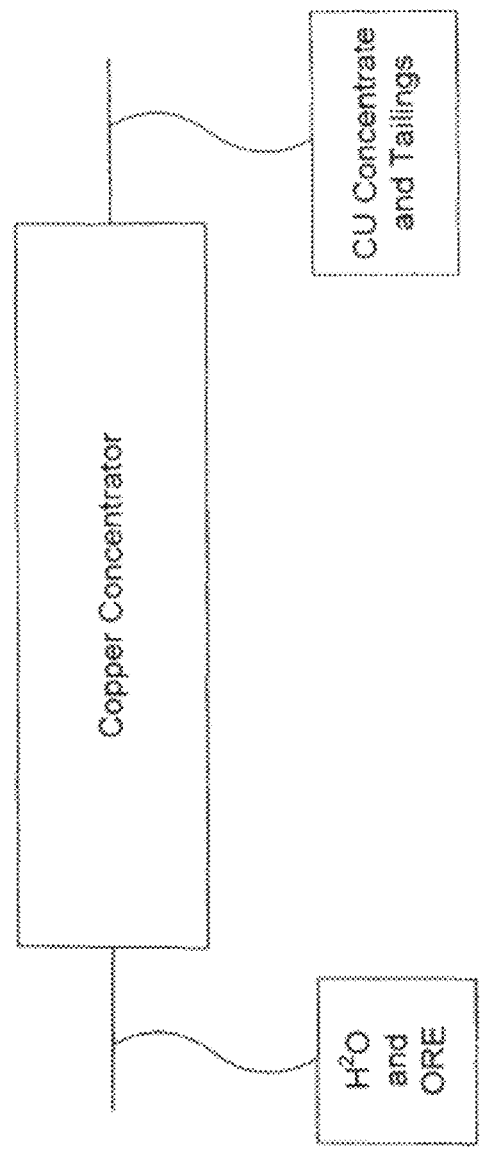
FIGURE 1a: Mineral Extraction Processing System – Prior Art

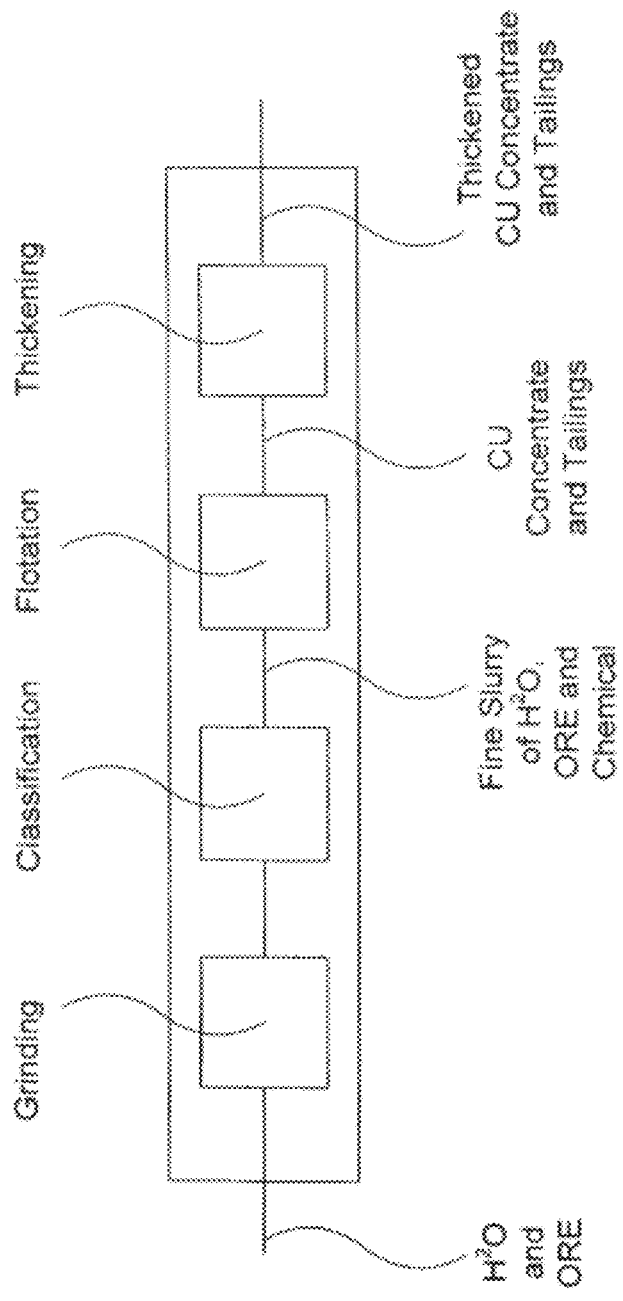
FIGURE 1b – Prior Art

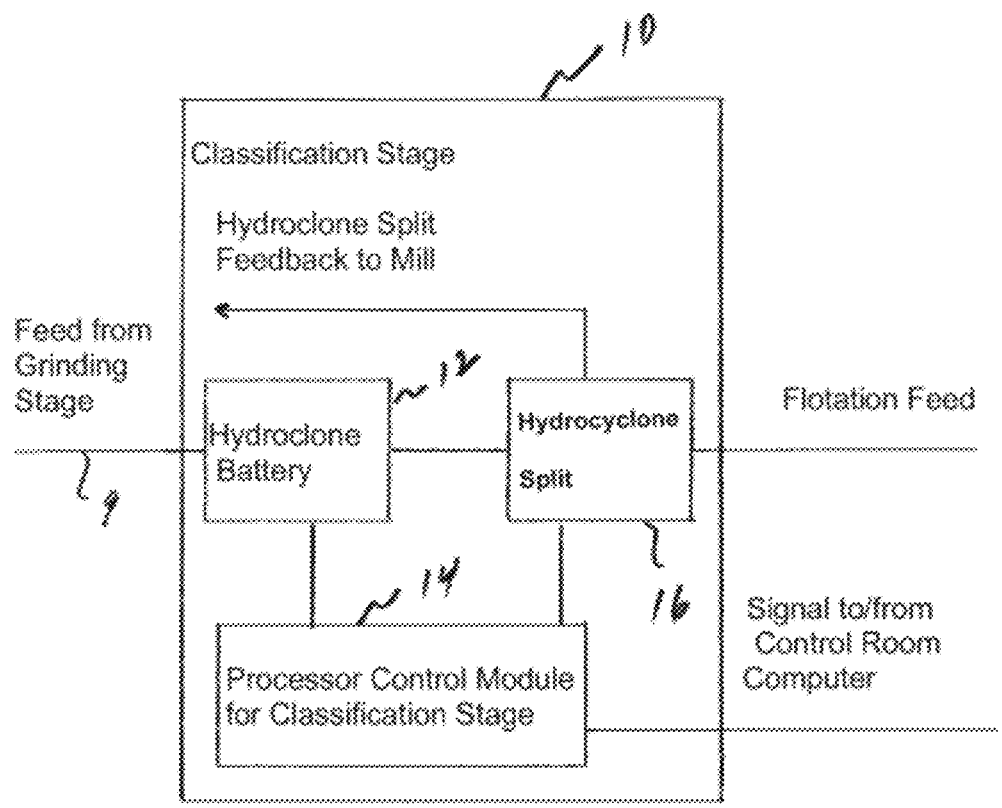
FIGURE 2: Classification Stage

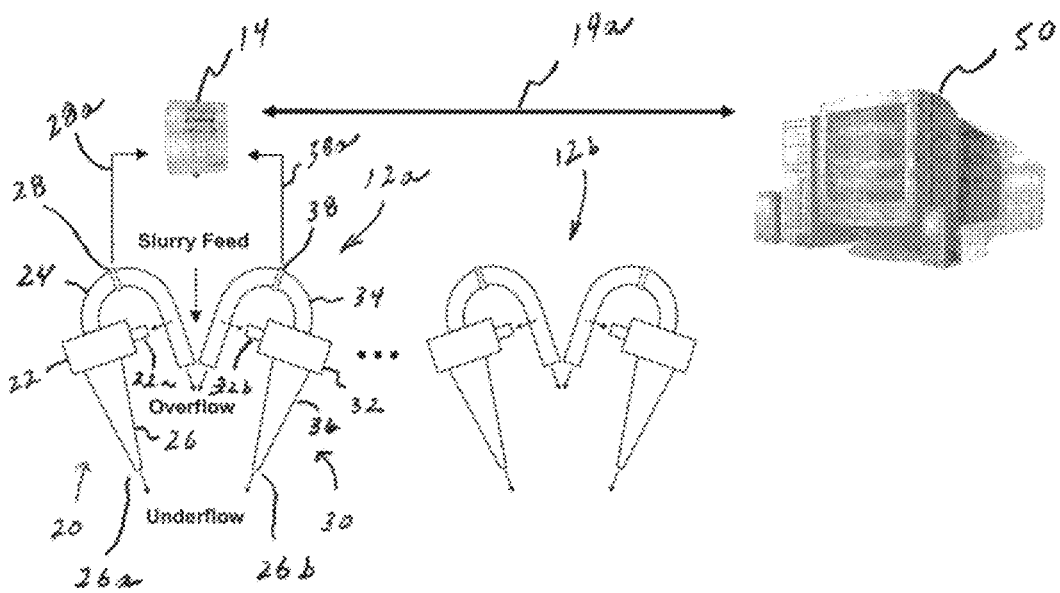
Figure 3a
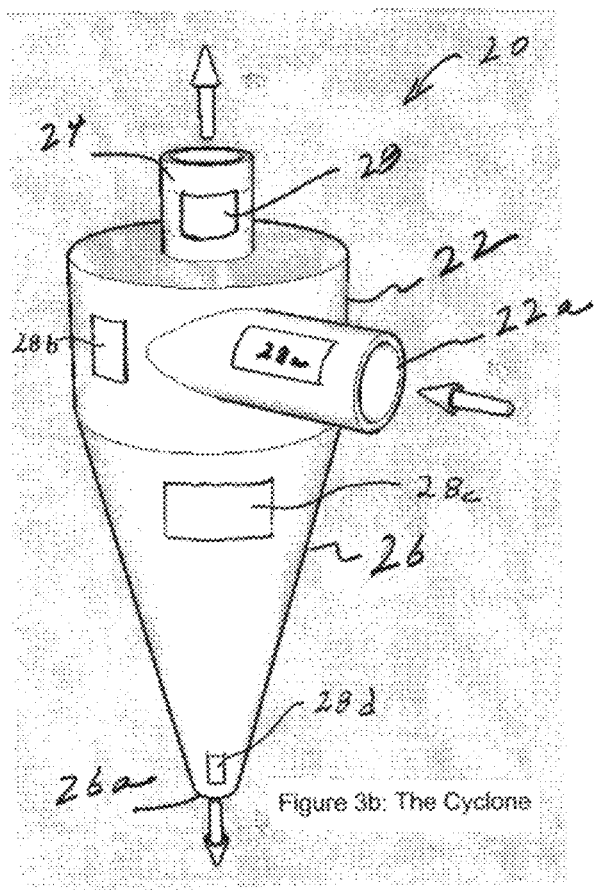
Figure 3b: The Cyclone

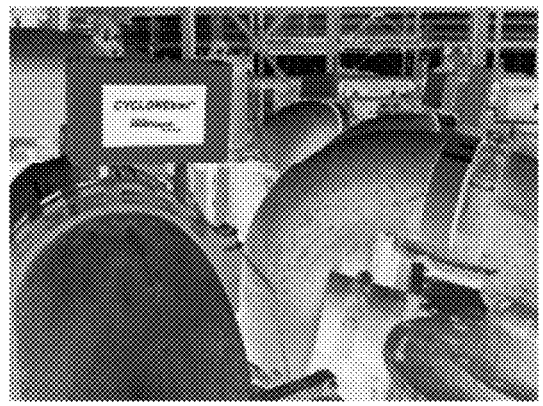
Figure 3c: Oversize detection system on hydrocyclone overflow line

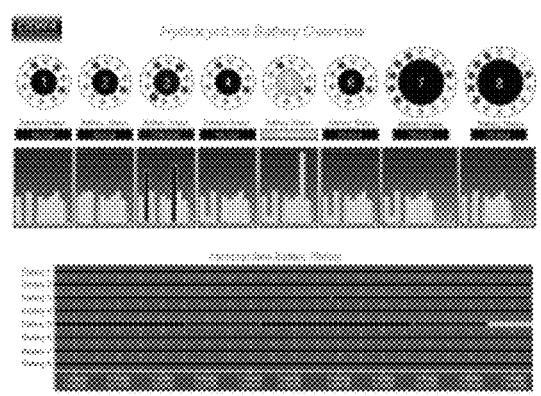
Figure 3d: Control room display of real-time cyclone information

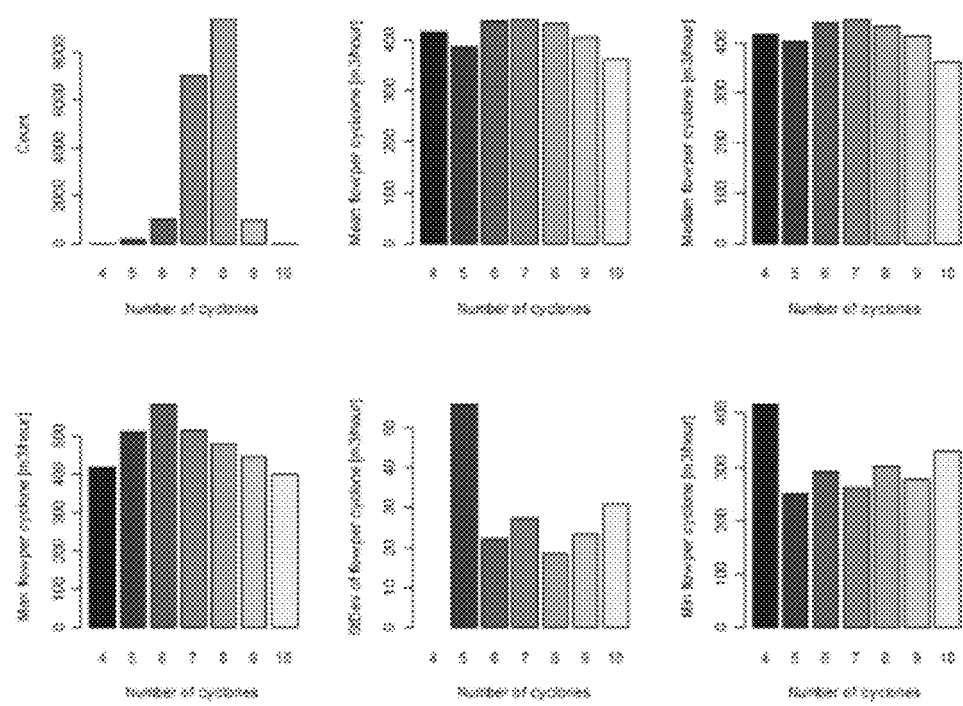
Figure 4: Basic cyclone flow data

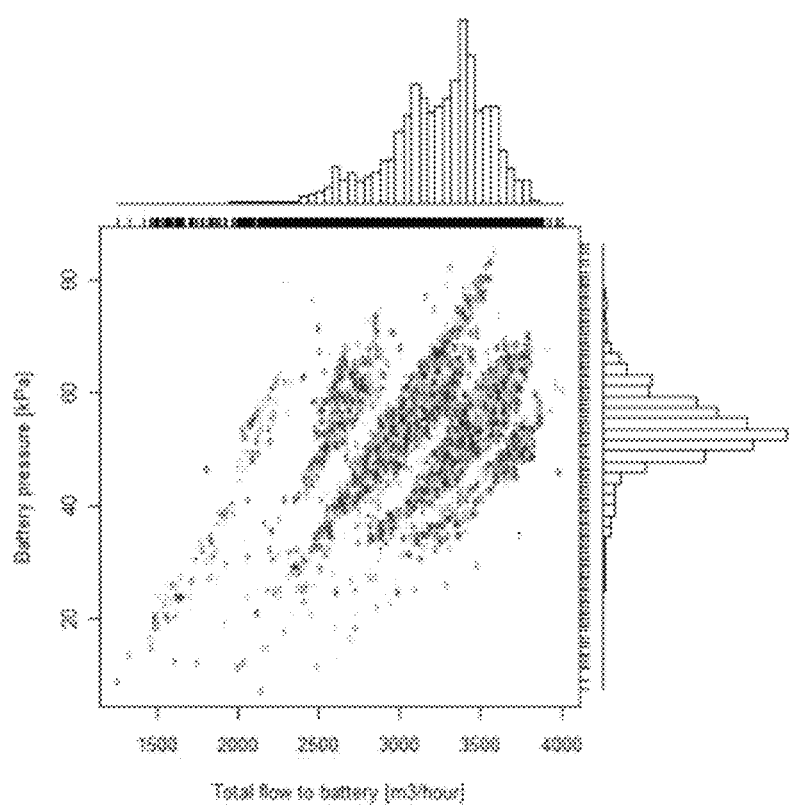
Figure 5: Pressure versus flow cross plot.

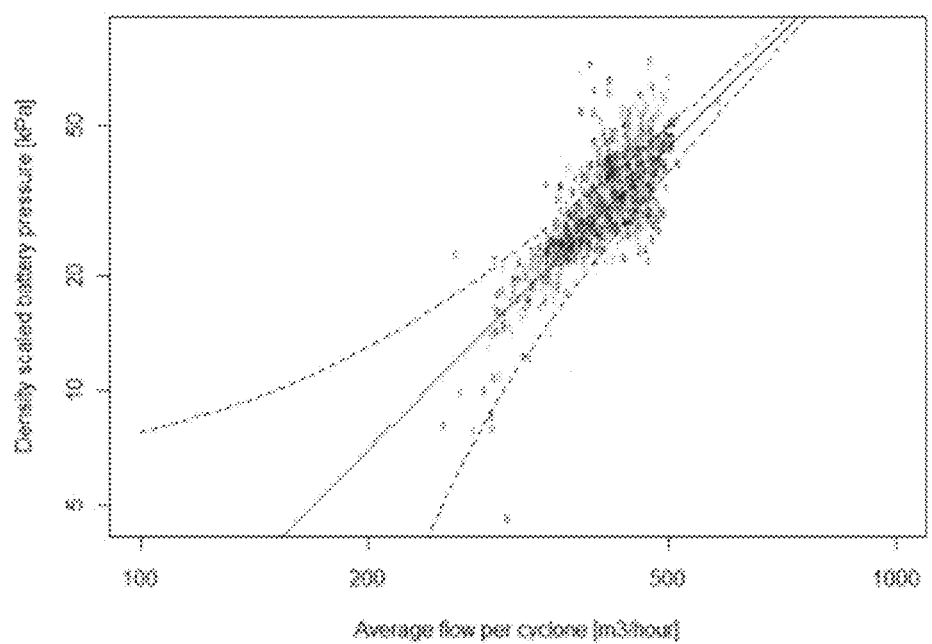
Figure 6: Flow performance curve of cyclones

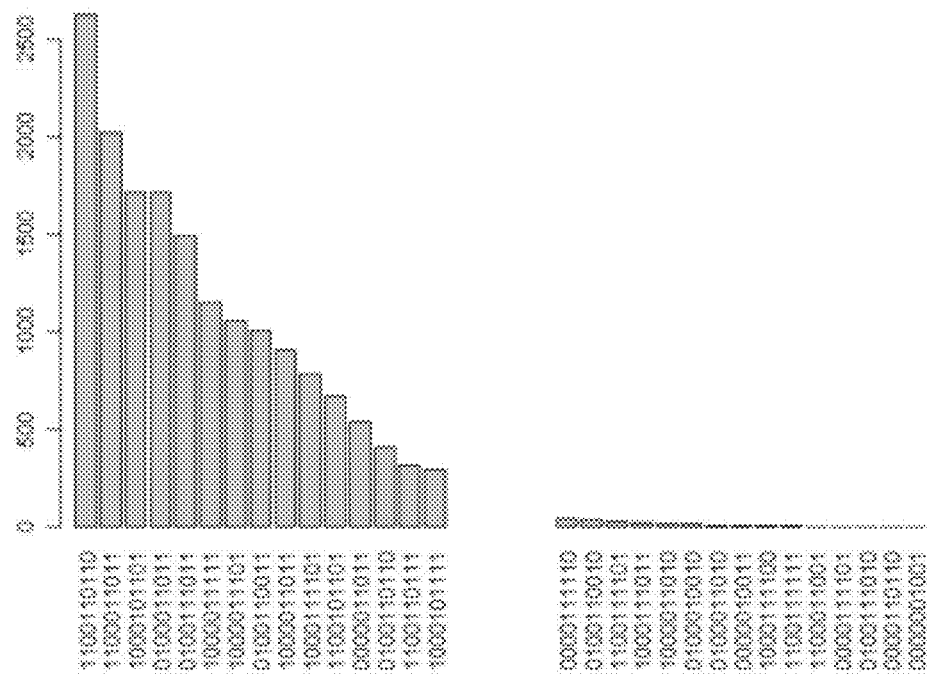
Figure 7: Cyclone combination counts

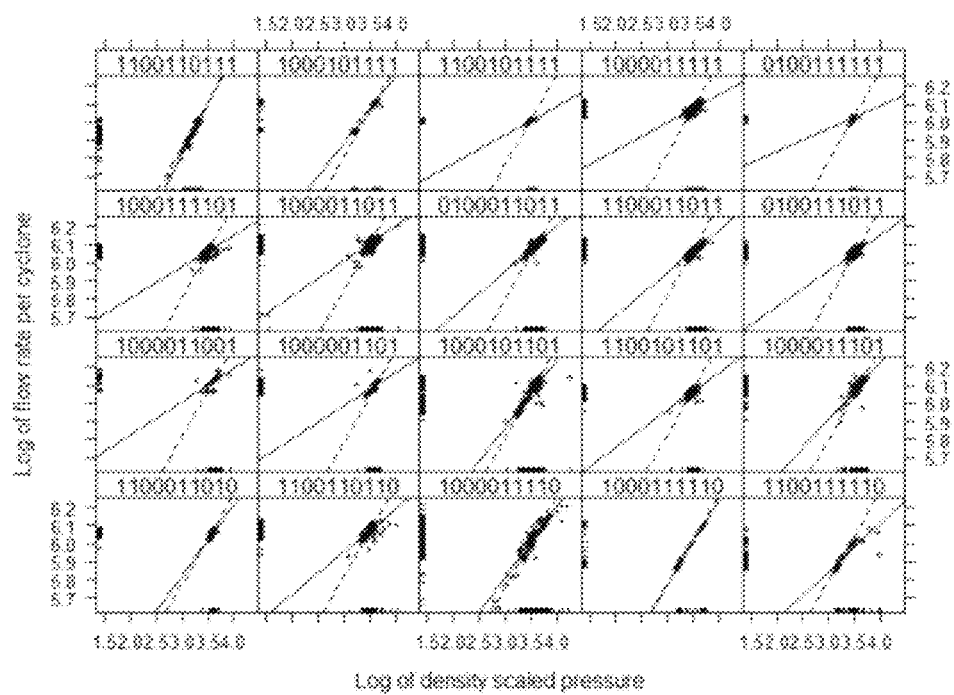
Figure 8: Individual cyclone combination performance plots

Figure 9: The Matrix Equation

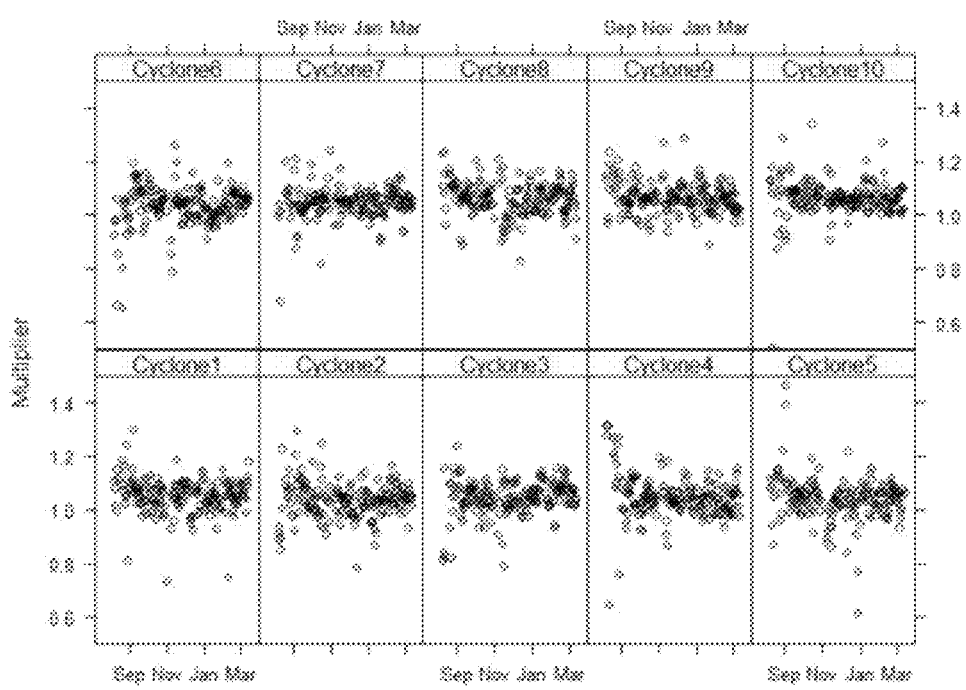
Figure 10: Cyclone multiplier versus time

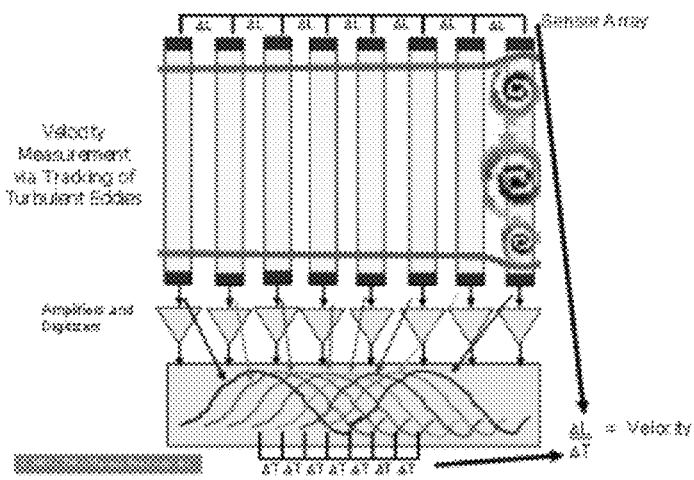
Figure 13: Illustration of stain induced in pipe walls by passing turbulent eddies, resulting in similar signals detected by sensor elements with time or phase differences, leading to velocity measurement

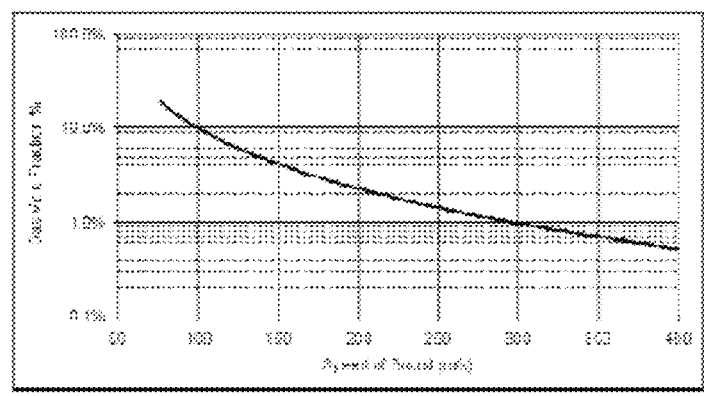
Figure 14: Example of relationship between gas volume fraction (entrained air bubbles) and speed of sound

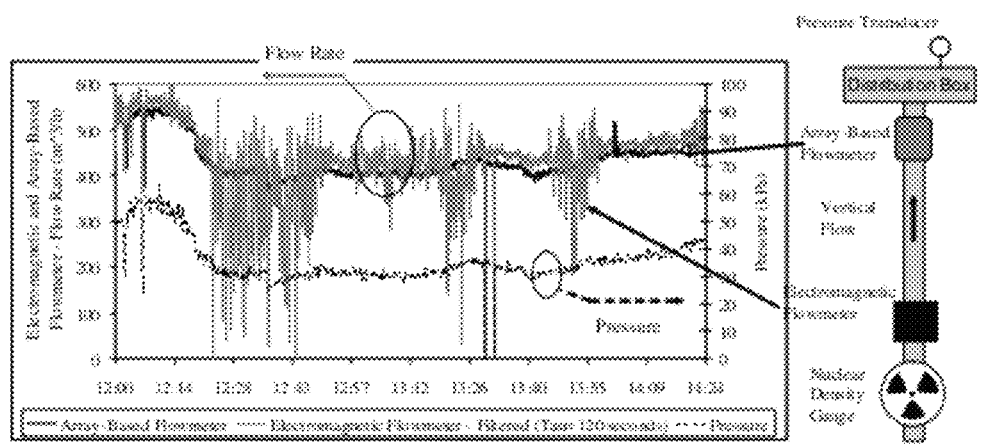
Figure 15: Comparison of readings from array-based flowmeter, electromagnetic flowmeter and pressure transducer.

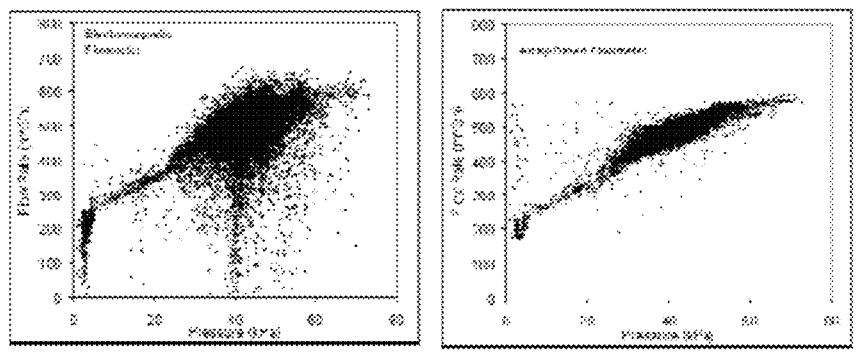
Figure 16a (Left): Crossplot of electromagnetic flowmeter readings versus pressure. Figure 16b (Right) Crossplot of array-based flowmeter readings versus pressure

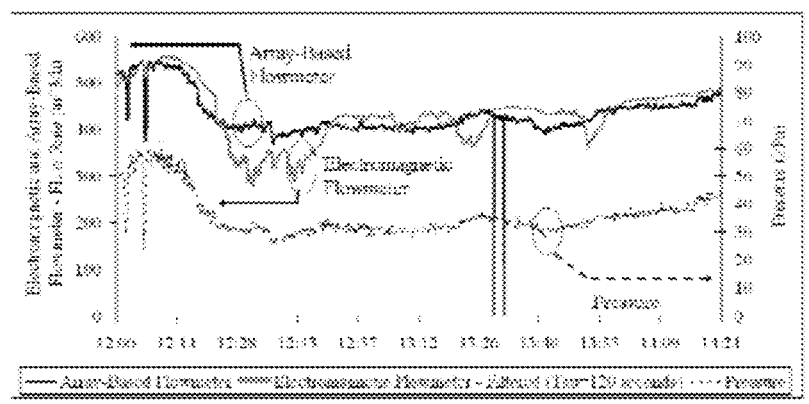
Figure 17: Comparison of readings from array-based flowmeter and pressure readings along with filtered reading from electromagnetic flowmeter (first

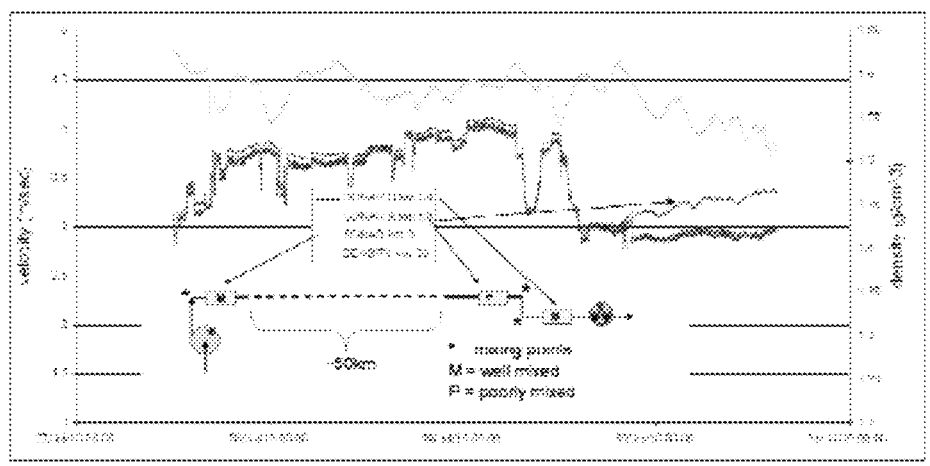
Figure 18: Stratification detection using 3 sonar flowmeters

Figure 19a (left) and Figure 19b (right): Difference in flowrate between two sonar flowmeters, and difference between two mag meters, all on the same 50 km pipeline. A sonar and mag are located close together at each end of the line.

PERFORMANCE MONITORING OF INDIVIDUAL HYDROCYCLONES USING SONAR-BASED SLURRY FLOW MEASUREMENT

CROSS-REFERENCE TO RELATED APPLICATIONS

This application corresponds to international patent application serial no. PCT/US2010/045178, filed 11 Aug. 2010, which claims benefit to provisional patent application Ser. No. 61/232,875, filed 11 Aug. 2009; Ser. No. 61/400,819, filed 2 Aug. 2010; and Ser. No. 61/370,154, filed 3 Aug. 2010, which are all incorporated by reference in their entirety.

This application is also related to PCT application serial no. PCT/US09/43438, filed 11 May 2009, which is incorporated by reference in its entirety.

BACKGROUND OF THE INVENTION

1. Field of Invention

This invention relates to a technique for monitoring the performance of individual hydrocyclones operating in a hydrocyclone battery; and more particularly, this invention also relates to a technique for monitoring the performance of individual hydrocyclones operating in a hydrocyclone battery using SONAR-based flow meter VF/GVF metering in a mineral extraction processing system, including extracting a mineral from ore.

2. Description of Related Art

In many industrial processes the sorting, or classification, of product by size is critical to overall process performance. A minerals processing plant, or beneficiation plant, is no exception. In the case of a copper concentrator as shown in FIG. 1a, the input to the plant is water and ore (of a particular type and size distribution) and the outputs are copper concentrate and tailings. The process consists of a grinding, classification, floatation, and thickening, as shown in FIG. 1b. The grinding and classification stage produces a fine slurry of water and ore, to which chemicals are added prior to being sent to the flotation stage. Once in the flotation stage, air is used to float the copper mineral while the gange (tailings) is depressed. The recovered copper is cleaned and dried. The tailings are thickened and sent to the tailings pond. The classification stage is critical to the performance of two areas of the process. These areas are the grinding throughput and flotation recovery, grade and throughput.

Grinding Operation

A grinding operation may include a screens and crusher stage and a mill stage, that is typically configured mills in closed circuit with a hydrocyclone battery. A hydrocyclone is a mechanical device that will separate a slurry stream whereby the smaller particles will exit out the overflow line and the larger particles will exit out the underflow line. The overflow is sent to the flotation circuit and the underflow is sent back to the mill for further grinding. A collection of these devices is called a battery. A hydrocyclone will be sized based on the particular process requirements. The performance of the hydrocyclone is dependent on how well it is matched to the process conditions. Once the proper hydrocyclone has been chosen and installed, it must be operated within a specific range in order to maintain the proper split between the overflow and the underflow. The split is dependent on slurry feed density and volumetric flow into the device. A typical control system will use a combination of volumetric flow, feed density and pressure across the hydrocyclone to control the split. Because of the harsh environmental and process conditions all of these measurements suffer from maintenance and performance issues. This can result in reduced classification performance and reduced mill throughput. Flotation performance is highly dependent on the particle size distribution in the feed which comes from the battery overflow, thus it is dependent on the hydrocyclone classification performance. The mill throughput is highly dependent on the circulation load which comes from the battery underflow. Traditionally hydrocyclone performance has been determined by evaluating manually collected samples from the consolidated hydrocyclone battery overflow stream. This technique is time consuming; the accuracy is subject to sampling techniques; the sample is a summation of all the hydrocyclones from the battery; and has a typical 24 hour turnaround time. Therefore it is not possible to implement a real time control algorithm to monitor, control, and optimize the each individual hydrocyclone.

Real time monitoring of each individual hydrocyclone would provide the ability to track the performance of individual hydrocyclones. This would enable the following:

The detection of hydrocyclones that require maintenance or have become plugged.

The detection of operational performance instabilities that cause extended periods of roping or surging.

The detection of chronic problems with curtain hydrocyclones.

Tighter classification control with changing throughput demands and feed densities.

Increased up time or availability of the hydrocyclone battery.

Another common problem with hydrocyclone monitoring is reliably determining if a feed gate valve is open or closed. This is typically done using two micro switches. One switch indicates the valve is in the open position and the other switch indicates it is in the closed position. These switches are typically unreliable and require constant maintenance. A reliable maintenance free method is needed.

SUMMARY OF THE INVENTION

In its broadest sense, the present invention provides a new and unique method and apparatus to track the flow performance of individual cyclones operating in parallel on a cyclone battery.

According to some embodiments of the present invention, the apparatus may comprise at least one module configured to respond to signals containing information about sound propagating through a slurry flowing in parts, including overflow pipes, of cyclones operating in parallel on a cyclone battery, and to determine the performance of individual cyclones based at least partly on the information contained in the signals. The apparatus may take the form of a signal processor or signal processor module, and the at least one module may take the form of a processor and at least one memory including a computer program code, where the processor and at least one memory are configured to cause the apparatus to implement the functionality of the present invention, e.g., to respond to signals containing information about sound propagating through the slurry flowing in the parts, including the overflow pipes, of the cyclones operating in parallel on the cyclone battery, and to determine the performance of the individual cyclones based at least partly on the information contained in the signals.

The apparatus may also include one or more of the following features:

For example, according to some embodiments of the present invention, each signal may contain information about sound propagating through the slurry flowing in a respective overflow pipe of a respective cyclone.

According to some embodiments of the present invention, the at least one module may be configured to: respond to signaling containing information about a battery flow rate, battery pressure, feed density, and cyclone status as indicated by individual gate valve positions of respective cyclones, the cyclone status including the state of the cyclone battery in terms of the number of the cyclones in operation; decompose average flow per cyclone versus density scaled pressure by actual cyclone combinations open to flow; and determine the performance of such cyclone combinations.

According to some embodiments of the present invention, the at least one module may be configured to determine a cyclone performance curve based at least on the following equation:

$$\log(q) = a \times \log\left(\frac{p}{\rho}\right) + b, \quad (1)$$

where q is the cyclone flow rate, p the battery pressure, ρ the slurry density, and a is the slope, and b is the intercept.

According to some embodiments of the present invention, the at least one module may be configured to derive an individual cyclone performance whenever there are more combinations in a given period of time than there are individual cyclones.

According to some embodiments of the present invention, the signals may be provided by sensors, each sensor being mounted on a respective overflow pipe of a respective cyclone and configured to respond to sound propagating in the respective overflow pipe of the respective cyclone. Each sensor may take the form of a sonar-based clamp-around flow meter, and the sonar-based clamp-around flow meter may be configured to respond to a strain imparted by the slurry made up of water and fine particles flowing in the respective overflow pipe of the respective cyclone, and provide a respective signal containing information about sound propagating through the slurry flowing in the respective overflow pipe of the respective cyclone. Each signal may be an amplitude-based time domain signal and has a frequency spectrum signature, and the at least one module may be configured to respond to the signals and determine the performance of each cyclone and take real time control action to optimize the performance of the cyclone battery. The at least one module may be configured to selectively open and close one or more of the cyclones based at least partly on the information contained in the signals.

According to some embodiments of the present invention, the at least one module may be configured to perform some combination of the following:

detect course material, "rocks", in the overflow pipe; or detect "oversize" material in an overflow stream; or detect a flowing/non-flowing cyclone condition of the respective cyclone; or based on a detected performance of individual cyclones, employ a control strategy to maximize a cyclone battery availability and reduce the amount of large particle discharge sent to a flotation stage.

According to some embodiments of the present invention, the at least one module may be configured to detect course material, "rocks", including particles whose size are greater than about 0.1" in diameter, in the overflow pipe by processing the amplitude-based time domain signal and determining when a rock impacts the wall of the pipe, including by first taking the acceleration of the amplitude-based time domain signal and then processing that with a peak detection algorithm. The at least one module may also be configured to detect "oversize" material, including oversize material defined by a size distribution that is greater than a design set point in the overflow stream, in the overflow pipe by feeding a neural net based algorithm the measured real time frequency spectrum, where the neural net based algorithm has been trained to recognize one spectrum that represents a size distribution that is representative of the design point as well as another spectrum that does not. The at least one module may also be configured to detect the flowing/non-flowing cyclone condition, where a feed to the respective cyclone is controlled with a gate valve, by detecting that there is not flow to the respective cyclone when a gate valve is closed, and by detecting that the feed flow enters the respective cyclone when the gate valve is open, where the neural net based algorithm has been trained to recognize the spectrum that represents both a flowing condition and a non-flowing condition. The at least one module may also be configured to employ a control strategy to maximize the cyclone battery availability and reduce the amount of large particle discharge sent to flotation, where cyclone battery feed flow, feed density, and pressure are used to control the number of cyclones that are flowing at any given time, using an open loop process, by monitoring the performance of individual cyclones and doing one or more of the following:

turning off one or more cyclones that are performing poorly; or optimizing the number of cyclones that are flowing for a given plant operating condition; or developing a predicative maintenance schedule by trending individual cyclone performance over time.

According to some embodiments of the present invention, the at least one module may be configured to provide an output signal containing information that identifies an on-off status of individual cyclones, a qualitative alarm that identifies the severity of rock events detected, and a quantitative measure of the number rocks detected vs time.

According to some embodiments of the present invention, the at least one module may be configured to provide an output signal containing information to take corrective action, including shutting off an offending cyclone, or adjusting other operating parameters such as changing flow rate, feed density, or battery pressure based at least partly on optimize cyclone performance by identifying poorly performing cyclones, or some combination thereof.

According to some embodiments of the present invention, the at least one module may provide an output signal containing information either to allow an operator to optimize cyclone performance, including real-time cyclone information for displaying on a control room display, or to control directly the operation of the cyclones in the cyclone battery to optimize cyclone performance.

According to some embodiments of the present invention, the at least one module may be configured to determine the presence of particles in various general size classes based at least partly on the fact that each size class has a unique acoustic signature.

According to some embodiments of the present invention, the at least one module may be configured to identify an abnormally high fraction of particles larger than a separation size, but smaller than a course material or "rock" size, including to monitor the amount of oversize material in real-time to further cyclone performance optimization, to increase overall mineral recovery in a concentrator plant, and/or to reduce energy consumption in a grinding process.

According to some embodiments of the present invention, the apparatus, including a non-invasive acoustic-based passive monitoring system, may comprise cyclones, sensors and a signal processor. The cyclones may be configured in parallel to form a cyclone battery in order to process a slurry, each cyclone having an overflow pipe for providing some portion of the slurry flowing in the cyclone battery. Each sensor may be configured to mount on a respective overflow pipe of a respective cyclone, to respond to sound propagating through the slurry flowing in the respective overflow pipe of the respective cyclone, and to provide a respective signal containing information about the sound propagating through the slurry flowing in the respective overflow pipe of the respective cyclone. The signal processor may be configured to respond to respective signals from the sensors and determine the performance of individual cyclones based at least partly on the information contained in the respective signals.

According to some embodiments of the present invention, the sensor may be mounted on the top of the overflow pipes, or mounted on the bottom of the overflow pipes, or pairs of sensors including a first sensor pair with one sensor mounted on the top of one overflow pipe, and another sensor mounted on the bottom of the one overflow pipe, and including a second sensor pair with one sensor mounted on the top of another overflow pipe, and another sensor mounted on the bottom of the other overflow pipe. The scope of the invention is not intended to be limited to the number of sensors mounted on the overflow pipes, or the location of the sensors mounted on the overflow pipes. For example, embodiments are envisioned using sensors mounted on the parts of the cyclones that may include some combination of an inlet portion, a cylindrical section, a conical base section, an overflow pipe, or the underflow outlet. Further, embodiments are also envisioned using sensors mounted partially or substantially around the overflow pipe, as well as down the length of the overflow pipe, as well as mounted partially or substantially around other parts of the cyclones, including the inlet portion, the cylindrical section, the conical base section, or the underflow outlet, down the length of one or more of these other parts, or some combination of the above.

According to some embodiments of the present invention, the apparatus, including the non-invasive acoustic-based passive monitoring system, may include one or more of the features set forth above.

According to some embodiments of the present invention, the method may comprises responding to signals containing information about sound propagating through a slurry flowing in overflow pipes of cyclones operating in parallel on a cyclone battery, and determining the performance of individual cyclones based at least partly on the information contained in the signals. The method may also include one or more of the features set forth above.

According to some embodiments of the present invention, the apparatus may also take the form of a computer-readable storage medium having computer-executable components for performing the steps of the aforementioned method. The computer-readable storage medium may also include one or more of the features set forth above.

Consistent with that described herein, and as one skilled in the art would appreciate, in operation the hydrocyclone battery as a classification device determines both the recirculating load in a communition circuit as well as the particle size passed on to beneficiation. Poor cyclone operation is believed to be the commonest cause of grinding inefficiencies. Whereas the advantages of hydrocyclones are obvious to anyone their apparent simplicity makes their performance difficult to monitor on line. Significant departures from the optimum do occur and are often not apparent to the operators. See *Mineral communition circuits*, their operation and optimization. JKMRC Technology Transfer.

According to the present invention, a path is set forth towards improved monitoring of (individual) hydrocyclones in real time using just the total flow rate to the cyclone battery, the cyclone battery pressure and the state of the cyclone battery in terms of number of cyclones in operation. No additional new equipment is necessary. Such an approach has become feasible with the introduction of reliable, accurate slurry flow meters that are not subject to wear because of their clamp around nature. See O'Keefe C. V., Maron R. M., Gajardo L., (2007), *Application of passive sonar technology to minerals processing applications*. MAPLA 2007, as well as O'Keefe C. V., Maron R. J., Rothman P. J., Poplawski J., *Description of Non-Intrusive Sonar Array-Based Technology and its Application to Unique and Difficult Slurry and Paste Flow Measurements*, Presented at PASTE 2008, Kaskane, Botswana, May 2008.

BRIEF DESCRIPTION OF THE DRAWING

The drawing includes FIGS. 1-19, which are not drawn to scale, as follows:

FIG. 1a is a block diagram of a mineral extraction processing system in the form of a copper concentrator that is known in the art.

FIG. 1b is a block diagram showing typical processing stages of a mineral extraction processing system that is known in the art.

FIG. 2 is a block diagram showing a classification stage according to some embodiments of the present invention.

FIG. 3a is a diagram showing apparatus according to some embodiments of the present invention, including a cyclone battery, sensors, a signal processor and a remote computer processor.

FIG. 3b is a diagram showing a cyclone a cyclone having a sensor arranged on an overflow pipe according to some embodiments of the present invention.

FIG. 3c is a diagram showing an oversized detection system on a hydrocyclone overflow line according to some embodiments of the present invention.

FIG. 3d is a diagram showing a control room display of real-time cyclone information according to some embodiments of the present invention.

FIG. 4 is a diagram showing six (6) graphs having basic cyclone flow data according to some embodiments of the present invention, including a graph showing count versus a number of cyclones, a graph showing mean flow per cyclone versus a number of cyclones, a graph showing medium flow per cyclone versus a number of cyclones, a graph showing maximum flow per cyclone versus a number of cyclones, a graph showing standard deviation (StDev) of flow per cyclone versus a number of cyclones, and a graph showing minimum flow per cyclone versus a number of cyclones.

FIG. 5 is a cross plot of pressure versus flow according to some embodiments of the present invention, including a graph showing a battery pressure versus total flow to the battery.

FIG. 6 is a flow performance curve of cyclones according to some embodiments of the present invention, including a graph showing a density scaled battery pressure versus average flow per cyclone.

FIG. 7 is a graph showing cyclone combination counts according to some embodiments of the present invention.

FIG. 8 shows performance plots of individual cyclone combinations according to some embodiments of the present invention, including graphs showing log of flow rate per cyclone versus log of density scaled pressure.

FIG. 9 shows a matrix equation for solving using, e.g., singular value decomposition (SVD) according to some embodiments of the present invention.

FIG. 10 shows graphs of a cyclone multiplier versus time for 10 cyclones labeled 1 through 10 according to some embodiments of the present invention.

FIG. 13 is an illustration of strain induced in pipe walls by passing turbulent eddies, resulting in similar signals detected by sensor elements with time or phase differences, leading to velocity measurement according to some embodiments of the present invention.

FIG. 14 shows a basic operating principle for volumetric flow measurement in the form of a graph of gas void fraction % versus speed of sound (m/sec), as an example of a relationship between gas volume fraction (entrained air bubbles) and speed of sound, the understanding of which may be used for implementing some embodiments of the present invention.

FIG. 15 shows a basic operating principle related to feed to a hydrocyclone battery and screen in the form of a comparison of readings from an array-based flowmeter, electromagnetic flowmeter and a pressure transducer, the understanding of which may be used for implementing some embodiments of the present invention.

FIG. 16 shows a basic operating principle related to feed to a hydrocyclone battery and screen in the form of a graph showing a crossplot of electromagnetic flowmeter readings versus pressure, and a graph showing a crossplot of array-based flowmeter readings versus pressure, the understanding of which may be used for implementing some embodiments of the present invention.

FIG. 17 shows a basic operating principle related to feed to a hydrocyclone battery and screen in the form of a comparison of readings from an array-based flowmeter and pressure readings along with a filtered reading from an electromagnetic flowmeter, the understanding of which may be used for implementing some embodiments of the present invention.

FIG. 18 shows a basic operating principle related to feed to a hydrocyclone battery and screen in the form of graphs of velocity versus and density versus time related to stratification detection using 3 sonar flowmeters, the understanding of which may be used for implementing some embodiments of the present invention.

DETAILED DESCRIPTION OF BEST MODE OF THE INVENTION

Figure 11A:
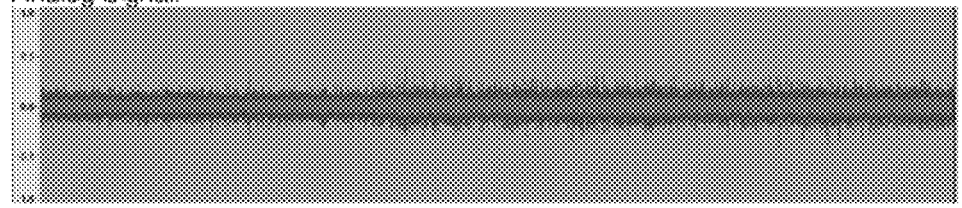
FIG. 11 shows three graphs of an analog signal from a sensor used for detection of course material ("Rock") reporting to an overflow pipe according to some embodiments of the present invention, including a graph of the analog signal, a graph of post processed acceleration related to the analog signal, and a graph of peak detection related to the analog signal.

In general, the present invention provides a new and unique technique to track the flow performance of individual cyclones operating in parallel on a single battery. The method can use battery flow rate, battery pressure, feed density and cyclone status as indicated by the cyclone's individual gate valve positions. By decomposing average flow per cyclone versus density scaled pressure by actual cyclone combinations open to flow the performance of such combinations can be found. Whenever there are more combinations in a given period of time than there are individual cyclones the individual cyclone performance can be derived. Detailed results of this method are provided herein for a single battery operating with 10 cyclones over a period of 238 days. Even though the distribution of cyclone combinations open to flow is highly skewed towards certain combinations, it is shown that individual cyclone performance does not degrade over time. During certain days of operation, however individual cyclone performance may well be 20% below or 20% above the rated capacity. Such deviations may indicate plugging of the underflow or a worn out cyclone apex respectively. Other explanations may also be found. It is also envisioned that further experience with individual cyclone performance tracking may also be helpful to develop even a better understanding of the root causes of deviations as set forth herein.

In particular, the hydrocyclone overflow stream contains particles that are less than or equal to the desired size. Since the hydrocyclone is not 100% efficient the overflow stream has a size distribution. This size distribution is an indicator of the operational performance of the hydrocyclone. The overflow stream is forced out the overflow pipe and is sent on to flotation. The overflow stream is a slurry made up of water and fine particles of ore. As the slurry moves through the overflow pipe it imparts a strain on the pipe wall. Very sensitive strain sensors are mounted on the outside wall of the overflow pipe to monitor the flow of slurry. The amplitude based time domain signal and the frequency spectrum signature from the sensors enable software algorithms to determine the performance of the hydrocyclone and to take real time control action to optimize the entire hydrocyclone battery performance.

The system is made up of at least one sensor mounted on some part or parts, including the overflow pipe, for each hydrocyclone in the battery. The at least one sensor is electrically connected to set of demodulation electronics. The demodulated signal is processed and sent to a control room computer for monitoring and display purposes. The control room computer will use this signal to determine which hydrocyclones to open and which ones to close. Other plant data such as hydrocyclone battery flow rate and pressure are also used to determine the optimized control strategy.

FIGS. 2-3*d*

In particular, FIG. 2 shows a classification stage according to the present invention and generally indicated as 10 that may form part of a mineral extraction processing system, like the one shown in FIGS. 1a and 1b for extracting minerals from ore. The classification stage 10 includes a hydrocyclone battery 12 that receives a feed from a grinding stage, as shown in FIG. 1b. The hydrocyclone battery 12 is configured to respond to signaling from a signal processor or processor control module 14, and provide an effluent, e.g., a fine slurry or slurry feed, to a flotation stage shown in FIG. 1b. The classification stage 10 also may include a hydrocyclone split 16 that receives the slurry from the hydrocyclone battery 12, and also may receive signaling from the signal processor or processor control module 14, and may provide some portion of the slurry back to the mill stage shown in FIG. 1b, and may also provide another portion of the slurry as a flotation feed to a flotation stage shown in FIG. 1b consistent with that described in the aforementioned PCT application serial no. PCT/US09/43438. The signal processor or processor control module 14 may also send to or receive from one or more signals with a control room computer 50 (see FIG. 3a). The new and unique technique according to the present invention to track the flow performance of individual cyclones operating in parallel on a single battery is described in relation to the hydrocyclone battery 12 (i.e. the single battery), the signal processor or processor control module 14 and the cooperation of these two components.

FIG. 3a shows the hydrocyclone battery 12 (i.e. the single battery), the signal processor or processor control module 14 and the cooperation of these two components according to some embodiments of the present invention. For example, the hydrocyclone battery 12 may include a first and second hydrocyclone pair 12a, 12b. The first hydrocyclone pair 12a includes a first hydrocyclone 20 and a second hydrocyclone 30. The first hydrocyclone 20 has a cylindrical section 22 with an inlet portion 22a for receiving via a feed pipe 9 the feed from the grinding stage shown in FIG. 1b, an overflow pipe 24 for providing one portion of the fine slurry or slurry feed to either the flotation stage shown in FIG. 1b, or the hydrocyclone split 16 shown in FIG. 2, and has a conical base section 26 with underflow outlet 26a for providing a remaining portion of the fine slurry or slurry feed. See also FIG. 3b, which shows, by way of example, the cyclone 20 in enlarged detail.

Similarly, the second hydrocyclone 30 has a cylindrical section 32 with an inlet portion 32a for receiving the feed from the grinding stage shown in FIG. 1b, an overflow pipe 34 for providing one portion of the fine slurry or slurry feed to either the flotation stage shown in FIG. 1b, or the hydrocyclone split 16 shown in FIG. 2, and has a conical base section 36 with underflow outlet 36a for providing a remaining portion of the fine slurry or slurry feed.

As one skilled in the art would appreciate, the first and second hydrocyclones 20, 30 classify, separate and sort particles in the feed from the grinding stage based at least partly on a ratio of their centripetal force to fluid resistance. This ratio is high for dense and course particles, and low for light and fine particles. The inlet portion 22a, 32a receives tangentially the feed from the grinding stage shown in FIG. 1b, and the angle and the length of the conical base section 26, 36 play a role in determining its operational characteristics, as one skilled in the art would appreciate.

According to some embodiments of the present invention, at least one sensor 28 is mounted on the overflow pipe 24 that is configured to respond to sound propagating in the overflow pipe 24 of the cyclone 20, and to provide at least one signal containing information about sound propagating through the slurry flowing in the overflow pipe 24 of the cyclone 20. Similarly, at least one corresponding sensor 38 is mounted on the overflow pipe 34 that is configured to respond to sound propagating in the overflow pipe 34 of the cyclone 30, and to provide at least one corresponding signal containing information about sound propagating through the slurry flowing in the overflow pipe 34 of the cyclone 30. The at least one sensors 28, 38 may take the form of a sonar-based clamp-around flow meter, which is known in the art consistent with that described below. The sonar-based clamp-around flow meters 28, 38 may be clamped in whole or in part around some portion of the overflow pipes 24, 34, and the scope of the invention is not intended to the manner or way in which the meters 28, 38 are configured on the overflow pipes 24, 34. For example, the at least one sensor or meter 28, 38 may be mounted on the top of the overflow pipes 24, 34, or the at least one sensor or meter 28, 38 may be mounted on the bottom of the overflow pipe 24, 34. Alternatively, a pair of at least one sensor or meter 28, 38 may be mounted on the overflow pipes 24, 34, e.g., with one sensor or meter mounted on the top of the overflow pipes 24, 34, and with another sensor or meter mounted on the bottom of the overflow pipe 24, 34. The scope of the invention is not intended to be limited to the number of sensors or meters mounted on the overflow pipe, or the location where the sensor(s) or meter(s) is mounted on the overflow pipe. For example, embodiments are envisioned using sensors or meters mounted partially or substantially around the overflow pipe, as well as down the length of the overflow pipe.

By way of example, in operation the sonar-based clamp-around flow meters 28, 38 may be configured to respond to a strain imparted by the slurry, e.g., made up of water and fine particles, flowing in the overflow pipes 24, 34 of the cyclones 20, 30, and provide the signals along signal paths or lines 28a, 38a containing information about sound propagating through the slurry flowing in the overflow pipes 24, 34 of the cyclones 20, 30.

According to some embodiments of the present invention, the apparatus may take the form the signal processor or processor control module 14 (FIG. 2), which is also shown in FIG. 3a, having at least one module configured to respond to the signals along the signal paths or lines 28a, 38a containing information about sound propagating through the slurry flowing in the overflow pipes 24, 34 of cyclones 20, 30 operating in parallel on the cyclone battery 12 (see also FIG. 2), and determine the performance of individual cyclones 20, 30 based at least partly on the information contained in the signals. The signal processor or processor control module 14 may also send to or receive from one or more signals along signal path or line 14a with the control room computer 50 (see FIG. 2). The signal processor or processor control module 14 may also be configured to respond to signaling containing information about a battery flow rate, battery pressure, feed density, and cyclone status as indicated by individual gate valve positions of respective cyclones, which are provided from the cyclone battery 12 (FIG. 2).

Furthermore, the scope of the invention is not intended to be limited to mounting the at least one sensor or meter on the overflow pipe. For example, embodiments are envisioned in which at least one sensor or meter 28a, 28b, 28c, 28d is mounted on another part of the cyclone or cyclone battery, or another part or pipe connected to the cyclone or cyclone battery, including the feed pipe 9, or the inlet portion 22a, 32a, or the cylindrical section 22, 32, or the conical base section 26, 36, or the underflow outlet 26a, 36a, or some combination thereof, as shown by way of example in FIG. 3b (which is not drawn to scale). Similar to that set forth with respect to the at least one sensor or meter 28, 38 described above, the scope of the invention is not intended to be limited to the number of sensors mounted on the another part of the cyclone or cyclone battery, or the other part or pipe connected to the cyclone or cyclone battery, or the location where the sensor, sensors, meter or meters is mounted on the another part of the cyclone or cyclone battery, or the other part or pipe connected to the cyclone or cyclone battery, For example, embodiments are envisioned using a sensor, sensors, a meter or meters mounted partially or substantially around the another part of the cyclone or cyclone battery, or the other part or pipe connected to the cyclone or cyclone battery, including mounted partially or substantially around the feed pipe 9, or the inlet portion 22a, 32a, or the cylindrical section 22, 32, or the conical base section 26, 36, or the underflow outlet 26a, 36a, or some combination thereof.

The SONAR-Based Clamp-Around Flow Meters 28, 38

The SONAR-based clamp-around flow meters 28, 38 is known in the art and disclosed by way of example in whole or in part in U.S. Pat. Nos. 7,165,464; 7,134,320; 7,363,800; 7,367,240; and 7,343,820, all of which are incorporated by reference in their entirety. For example, SONAR-based clamp-around flow meters 28, 38 may take the form of a SONAR-based VF/GVF-100 meter. The scope of the invention is also intended to include other types or kinds of SONAR-based VF/GVF meters either now known or later developed in the future that perform the same basic functionality of the SONAR-based VF/GVF meter as such functionality relates to implementing the present invention.

The scope of the invention is also intended to include using the SONAR-based clamp-around flow meters 28, 38 alone or in combination with a density meter, e.g. for providing signaling containing information about the feed density, disclosed by way of example in whole or in part in U.S. Pat. Nos. 7,165,464; 7,134,320; 7,363,800; 7,367,240; and 7,343,820. See also that disclosed in PCT application serial no. PCT/US09/43438, which is incorporated by reference in its entirety.

The Signal Processor or Processor Control Module 14

The functionality of the signal processor or processor control module 14 may be implemented using hardware, software, firmware, or a combination thereof. In a typical software implementation, the processor modules would include one or more microprocessor-based architectures having a microprocessor, a random access memory (RAM), a read only memory (ROM), input/output devices and control, data and address buses connecting the same. A person skilled in the art would be able to program such a microprocessor-based implementation to perform the functionality described herein without undue experimentation. The scope of the invention is not intended to be limited to any particular implementation using technology either now known or later developed in the future.

The Cyclone or Hydrocyclone 20, 30

The cyclone or hydrocyclone 20, 30 are known in the art, and the scope of the invention is not intended to be limited to any particular type or kind thereof either now known or later developed in the future.

The Classification Stage 10

By way of example, the present invention as it relates to the classification stage 10 is described in relation to the mineral extraction processing system shown, e.g., in FIGS. 1a and 1b, which takes the form of a copper concentrator, although the scope of the invention is not intended to be limited to any particular type or kind of mineral process or mineral extraction processing system either now known or later developed in the future.

The classification stage 10 may also include one or more elements, devices, apparatus or equipment that are known in the art, do not form part of the underlying invention, and are not disclosed herein or described in detail for that reason.

The scope of the invention re classification stage and/or hydrocyclone applications is not intended to be limited to the type or kind of mineral being processed, or the type of mineral process, either now known or later developed in the future. By way of example, the scope of the invention is intended to include hydrocyclone applications include Molybdenum, Lead, Zinc, Iron, Gold, Silver, Nickel, Fluorite, Tantalum, Tungsten, Tin, Lithium, Coal, as well as, e.g. diamonds, etc.

FIGS. 4-10

Figure 9:
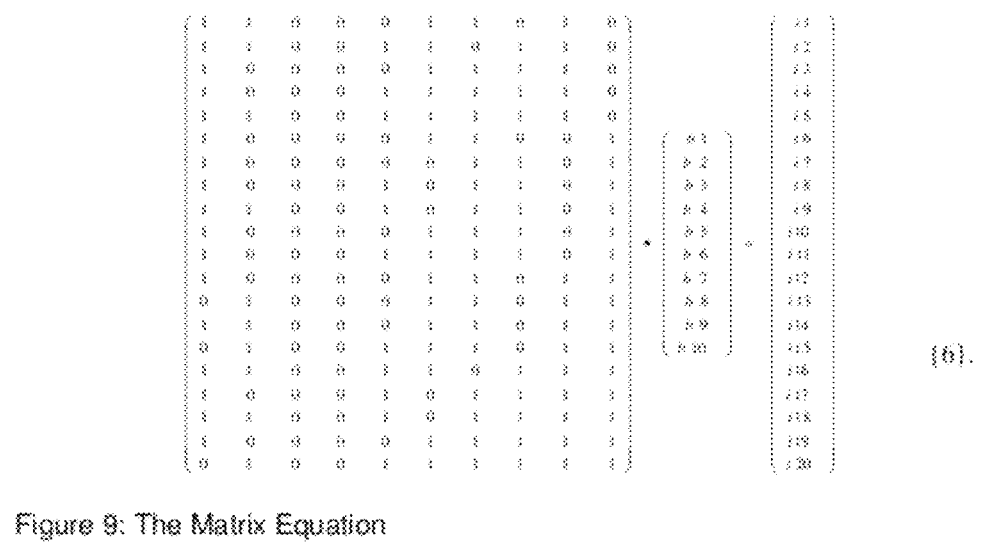

FIGS. 4-10 show by way of example a data processing technique according to some embodiments of the present invention to track the flow performance of individual cyclones operating in parallel on a single battery.

FIG. 4 presents, by way of example, some basic cyclone battery flow data. The summary flow data shows that the battery is operated such that most of the time 8 cyclones in the cyclone battery are flowing. The top left panel shows the count of number of cyclones open to flow. (Note that the horizontal axis provides the number of cyclones, not the cyclone number.)

Both the mean (top middle) and the median (top left) flow per cyclone is about 400 m3/hour with a standard deviation of about 20 to 30 m3/hour. When the number of cyclones open to flow is 4 or 5, the standard deviation and the range become larger. In particular, for 4 cyclones open it appears as if the maximum flow per cyclone (lower left) and the minimum flow per cyclone (lower right) are about equal. As one skilled in the art would appreciate, this is likely to occur because there is only one occurrence of 4 cyclones flowing. Hence the standard deviation (lower middle) for 4 cyclones flowing is undefined.

The Methodology

As one skilled in the art would appreciate, specifications of flow performance of cyclones as provided by manufacturers indicate that hydraulically a cyclone is much like a resistance to flow. (See Krebs Engineers, Tucson, Ariz., USA, Cyclone capacity curves.) On a log-log plot of pressure versus flow, the performance curve is a straight line with a slope of ½. This type of curve holds irrespective of the nature of the fluid. For both water and slurry the type curves are parallel. Thus a cyclone performance curve can be described as:

$$\log(q) = a \times \log\left(\frac{p}{\rho}\right) + b. \tag{1}$$

In this formula q is the cyclone flow rate, p the battery pressure, ρ the slurry density. The slope constant a equals ½ according to the manufacturers specifications whereas the intercept b varies with size and slurry density. A cross plot of battery pressure versus total flow to the battery indicates that at least 5 and possibly up to 7 different characteristic groups are present. FIG. 5 below shows by grey code and by digit the number of cyclones flowing. In the margins of the plot a histogram is provided. The regular spacing of pressure data is a result of the data historian hysteresis setting.

Evidently, the grouping may not entirely be due to the variation in cyclones open to flow. For instance, 6 cyclones open is found both at the far right as well as the far left of the plot. Had the grouping been the result of the number of cyclones open to flow, the groups would have likely shown a distinct grey level. In reality, the grey levels are spread out over the groups in what appears to be a random fashion. In a log-log plot of pressure divided by density versus average flow rate per cyclone, the grouping disappears as is shown below in FIG. 6.

In FIG. 6, a best fit line of slope ½ is drawn (solid line) as well as the 95% prediction interval lines (dashed lines). A very significant portion of the data points falls outside the 95% prediction intervals indicating that the ½ slope line is not applicable in at least those cases. Instead of using the number of cyclones, the performance of the battery per individual cyclone combination that is active can be investigated consistent with that described below.

Parallel Operation of Cyclones

In the case of N cyclones on a single battery, one can write N equations like equation {1} add those together and linearize:

$$\sum_{i=1}^{N} F_i \log\left(\frac{Q}{N_c}(1+\Delta_i)\right) \approx N_c \log\left(\frac{Q}{N_c}\right) + \sum_{i=1}^{N} \Delta_i F_i = \quad \{2\}$$

$$\log\left(\frac{p}{\rho}\right) \sum_{i=1}^{N} a_i F_i + \sum_{i=1}^{N} b_i F_i.$$

Here $F_1$ is a factor indicating the status of a particular cyclone, taken to be 1 in case it is open and 0 when the cyclone is closed. Q is the total flow to the battery $N_c$ is the number of cyclones open to flow. Since not all cyclones will be flowing at exactly the mean flow per cyclone $\Delta_i$ gives the relative deviation of the average which is assumed to be small enough to allow for the linearization applied. The other symbols retain their meaning from the previous equation. By definition $N_c$ is equal to the sum over $F_i$. In the case of ideal, equal cyclones all conforming to the manufacturer's specification all $a_i$ slope coefficients will equal ½, and all $\Delta_i$ are zero. In that case equation {2} simplifies to:

$$\log\left(\frac{Q}{N_c}\right) = \frac{1}{2} \log\left(\frac{p}{\rho}\right) + b. \quad \{3\}$$

This is in effect the equation that describes the type curves in the manufacturer's specifications. In reality it is unlikely that the parallel operation of cyclones will be ideal. Therefore as a practical model we will use:

$$\log\left(\frac{Q}{N_c}\right) = \frac{1}{2} A \log\left(\frac{p}{\rho}\right) + B. \quad \{4\}$$

The coefficients A and B are regression coefficients equal to:

$$A = \frac{2}{N_c} \sum_{i=1}^{N} a_i F_i \quad \{5\}$$

$$B = \frac{1}{N_c} \sum_{i=1}^{N} (b_i - \Delta_i) F_i.$$

As one skilled in the art would appreciate, one may now leave A free and find values for A and B by linear regression, or one may force A to be equal to 1 and solve only for the intercepts B.

Results and Discussion

As a first result, one may count the number or occurrences of each cyclone combination. For a 15 day period on this battery of 10 cyclones 45 different combinations occurred.

The distribution is shown in FIG. 7, where the 15 of the most frequently (the left panel) occurring and the 15 of least frequently (the right panel) occurring are plotted. Ideally this distribution would not tail off as fast as it does in practice. A uniform distribution would be advantageous in terms of cyclone wear. A symmetric load distribution over the cyclones could be advantageous in terms of cyclone performance.

For a 2-day period starting on, e.g., Tuesday as shown, one splits the cyclone performance curves by cyclone combination in effect. FIG. 8 shows how the log of flow rate per cyclone relates to the log of pressure divided by density.

Evidently, the wide scatter in the data points as is still visible in FIG. 6 is no longer present. Some outlier points do remain but just the process of splitting by cyclone combination, rather than by number or cyclones removes a lot of scatter.

The solid line in each panel is the regression line according to equation {4}. Compare the steepness of this line to the dashed line which is a line according to the idealized equation {3}, i.e. a slope of ½. This dashed line is drawn through the median of the data points. In all cases, the regression line has a slope lower than ½. This indicates an effective cyclone count higher than given by the cyclone valve states. A number of reasons could contribute to this:

1. Wrong cyclone states. The limit switches are 'sticking' falsely indicating the position of the valve thereby showing an 'OPEN' state for a cyclone that is in fact closed.

2. Leaking gate valves. In the case of partially closed valves there will be some flow passing through a cyclone without that cyclone being recorded as being open. The flow through a partially closed valve then resembles some portion of a full cyclone.

3. Inaccurate pressure data. As is obvious from FIG. 5, the battery pressure data is not of very high resolution. This may cause data points to show the same pressure at different flow rates thereby flattening the regression lines.

4. Inaccurate flow data. Although highly unlikely with the type of flow meter used in this case this has been a factor in the past that greatly complicates this kind of analysis.

5. Limited flow and pressure range. As is indicated by the marginal distribution of data plotted on the horizontal and vertical axes of each panel the whenever the data has a certain range and there are few outliers the dashed and solid lines overlay.

The last reason mentioned effectively boils down to stating that a linear regression appear to be fooled by all points effectively falling on top of each other which cause an error in the slope in the absence of even a single outlier. Therefore, one may fit for the intercept only forcing the slope (A=1) to be ½.

With the values of the vector B thus determined one can use the cyclone status as given in the panels of FIG. 8 as the state vector and assemble these into a matrix equation which would look like (for the data in FIG. 8).

In this matrix equation in FIG. 9, each row corresponds to a state vector, each column represents a cyclone. The individual coefficients of B are in given by $b_{1\ldots 10}$ whereas the 20 intercepts are given by $i_{1\ldots 20}$. Note that cyclones 3 and 4 are never in use during this period of time since all the entries in the columns 3 and 4 are zero. It may also happen that all entries in one or more column are always 1 indicating a cyclone that is always open. In the case of two columns that are equal then for the corresponding cyclones no individual state information can be obtained.

It is advantageous to use the known variance in the intercepts B in the process of solving for the individual cyclone flow coefficients. This is easily accomplished by weighing the intercepts and matrix coefficients with the inverse of the standard deviation of the intercepts B. As a result we obtain the uncertainty of the individual cyclone performance coefficients.

The matrix equation {6} shown in FIG. 9 is over determined (more rows than columns) and singular in this case because of the presence of two equal columns. One solves equations of the type {6} (see FIG. 9) by singular value decomposition (SVD) (See Press, W. H., Vetterling, W. T., Teukolsky, S. A., Flannery, B. P., Numerical Recipes in FORTRAN, The art of scientific computing, $2^{nd}$ edition, 1994, Cambridge University Press, Cambridge, UK. ISBN 0 521 43064 X) with automatic zeroing of small singular values in order to deal with the singularities introduced by linearly dependent columns. The result is a vector of flow coefficients B. The value of these flow coefficients can be tracked over time by repeated application of the above. In some cases there may be fewer rows than 20, in some cases as few as 10 or less. In the case of fewer rows (equations) than 10 no solution in the normal sense is possible. In the latter case the data of that particular day is skipped. The meaning of the flow coefficients thus derived should be clear, very low flow coefficients indicate that at a certain rate of flow a higher than normal pressure is required to drive the flow.

In practice the ratio of the individual cyclones flow coefficient to the manufacturers specified flow coefficient of the battery will be used to track the cyclone performance. In terms of the equation {5} one calculates multipliers $x_i$:

$$\frac{N_c B}{B} = \sum_{i=1}^{N} \frac{(b_i - \Delta_i)}{B} F_i = \sum_{i=1}^{N} x_i F_i. \quad (7)$$

Such multipliers are should be very close to 1 in the case of nearly identical and nearly ideal cyclones. Below in FIG. 10, the result of tracking the multiplier coefficients over a period of 238 days, in a moving average over 3 days is presented. Vertical bars indicate a one standard deviation uncertainty interval.

Evidently this battery of cyclones operates, in most cases, at near ideal conditions. There does not appear to be any steady degradation of cyclone performance over this period. Nonetheless there are certain periods where the multiplier flow coefficient deviates appreciably from 1. Such periods may indicate cyclone misbehaviour. Values of the multiplier below 1 indicating partial plugging whereas values larger than 1 may indicate a too high underflow.

Some Conclusions Based on Data Processing Technique

The following are some conclusions that may be drawn in relation to the data processing technique set forth above.

Simple cyclone battery data, i.e. pressure, density, flow rate and cyclone valve status can be used in a quantitative sense to track individual cyclone performance over long periods of time. The method developed here decomposes the pressure/density versus flow rate by actual cyclone combinations open to flow at any given time. The flow coefficients derived are thus combination specific.

In such cases that over a given period of time there are more cyclone combinations than there are individual cyclones the flow coefficients of the individual cyclones can be determined by singular value decomposition of an over determined, possibly singular system of linear equations.

This method of tracking individual cyclone performance relies on the abundant availability of accurate and reliable pressure/density and flow rate data. Accurate flow rate data has only become available in severe duty slurry service with the recent introduction of clamp-around flow meters that do not wear or drift with time.

By far the least reliable are the cyclone valve position indicators. Either mechanical limit switches or non-contact proximity indicators may both report false valve positions. The amount of data that had to be discarded because of undefined valve positions easily ranges from 10% to 20%. Work is now underway to develop a more reliable cyclone flow status indicator.

FIGS. 11-12

By way of example, a data processing technique according to some embodiments of the present invention related to the detection of course material ("rocks") reporting to the overflow pipe and hydrocyclone control strategies is described in relation to FIGS. 11-12.

According to some embodiments of the present invention, the system is used for four critical functions:

1. The detection of course material, "rocks", in the overflow stream
2. The detection of "oversize" material in the overflow stream
3. Flowing/non-flowing hydrocyclone condition
4. Based on the detected performance of the individual hydrocyclones a control strategy may be employed to maximize the hydrocyclone battery availability and reduce the amount of large particle discharge sent to flotation.

Detection of Course Material ("Rocks") Reporting to the Overflow

Figure 11B:
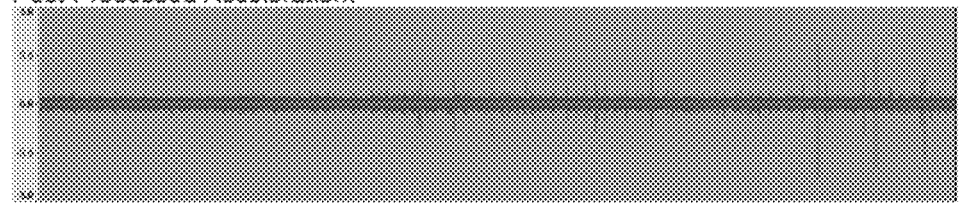
Figure 11C:
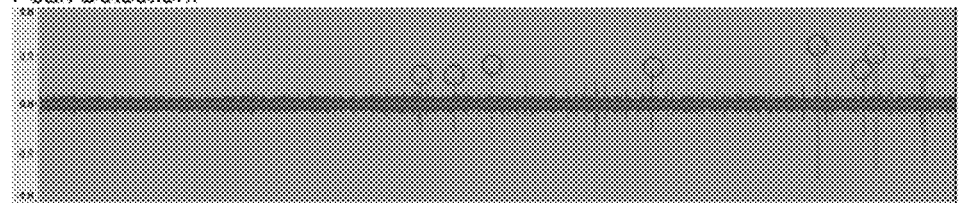

Course material, or "rocks", are defined as particles whose size are greater than 0.1" in diameter. As shown in FIG. 11, the analog time domain signal from the sensor is processed through an algorithm that determines when a rock impacts the wall of the pipe. See FIG. 11*a*. This is done by first taking the acceleration of the analog signal as shown in FIG. 11b and then processing that with a peak detection algorithm as shown in FIG. 11c.

Detection of Oversize Material Reporting to the Overflow

Figure 12A:
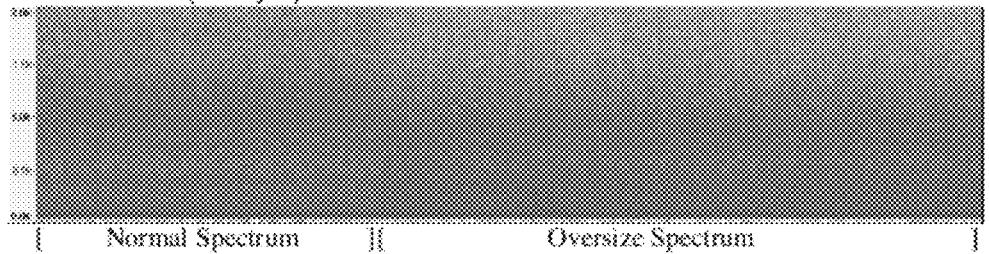
FIG. 12 shows two graphs of a real time frequency spectrum used for detection of course material ("Rock") reporting to an overflow pipe according to some embodiments of the present invention, including a graph showing a normal spectrum and an oversized spectrum, and a graph showing flowing and non-flowing condition.

Oversize material is defined as a size distribution that is greater than the design set point. This is determined by feeding a neural net based algorithm the measured real time frequency spectrum, as shown in FIG. 12. The neural net has been trained to recognize the spectrum that represents a size distribution that is representative of the design point as well as a spectrum that does not. See FIG. 12a

Flowing Versus Non-Flowing Hydrocyclone Condition

Figure 12B:
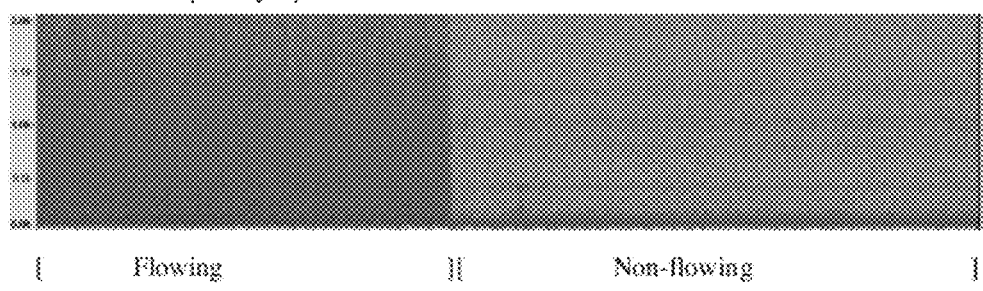

The feed to the hydrocyclone is typically controlled with a gate valve. When the gate valve is closed there is not flow to the hydrocyclone. When the gate valve is open then the feed flow enters the hydrocyclone. The neural net has been trained to recognize the spectrum that represents both a flowing condition and a non-flowing condition, as shown in FIG. 12b.

Hydrocyclone Control Strategy Using Real Time Performance Feedback

Hydrocyclone battery feed flow, feed density, and pressure are typically used to control the number of hydrocyclones that are flowing at any given time. This is done in an open loop manner. By monitoring the performance of individual hydrocyclones new control strategies may be employed. The following may be accomplished:
1. Turn off hydrocyclones that are performing poorly. The poor performance may be due to damage or wear. It may also be a transient instability in the hydrocyclone operating condition.
2. Optimize the number of hydrocyclones that are flowing for a given plant operating condition. By now having the performance feedback flow rate and density may be manipulated to maximize throughput and availability without sacrificing classification performance.
3. By trending individual hydrocyclone performance over time a predicative maintenance schedule can be developed. Therefore equipment availability can be maximized by reducing unscheduled shutdowns.

It is noted that FIGS. 11-12 show a very specific frequency range for the purpose of describing an example of the data processing technique. However, the scope of the invention is not intended to be limited to this specific frequency range shown in FIGS. 11-12, or any other frequency range either now known or later developed in the future. For example, embodiments of the present invention are envisioned using other frequency ranges, including a much higher frequency range.

FIGS. 13-19

The present invention set forth herein provides a new and unique non-invasive acoustic-based passive monitoring system that has been developed to provide real-time detection of the presence of large-size coarse material, ('rocks') in the overflow of individual hydrocyclones. The system provides:
information that identifies the on-off status of individual cyclones,
a qualitative alarm that identifies the severity of rock events detected, and
a quantitative measure of the number rocks detected vs time.

This previously-unavailable information provides operators with the ability optimize hydrocyclone performance by identifying poorly performing cyclones, and then take corrective action such as shutting off the offending cyclone, and/or adjusting other operating parameters such as changing flow rate, feed density, or battery pressure.

As described herein, hydrocyclones may be used in closed circuit grinding applications to separate particles based on size. This performance is typically represented by a partition curve, which defines a cut point, or separation size, that is the point on the curve for which 50% of the particles in the feed of that size report to the underflow, and 50% report to the overflow and thus pass to the flotation circuit.

Particles smaller than the separation size passing to the overflow pipe will have all the recoverable mineral liberated, thus available for recovery in the flotation circuit. Particles larger than the separation size passing to the overflow will have some unliberated mineral and thus will reduce the recovery of the flotation circuit.

As one skilled in the art would appreciate, a common problem in hydrocyclone operation occurs when particles much greater than the separation size (at least 10×), sometimes called 'rocks', are passed to the flotation circuit via the hydrocyclone overflow line. This causes two very costly problems; decreased mineral recovery in the flotation circuits, and additional maintenance due to accumulation of large solids in the bottom of flotation tanks.

According to some embodiments of the present invention, the acoustic-based cyclone monitoring system that has been developed is based on passive acoustic principles, and has some similarity to the well-known passive sonar flowmeter. Single and multi-phase flows produce unique acoustic signatures that provide valuable information about the composition of the flow. In multi-phase solid-liquid flows such as slurry flows in grinding circuits, the acoustic signature (amplitude, frequency, and phase) contains information concerning the size of particles being transported. Thus, acoustic analysis techniques can be used to determine the presence of particles in various general size classes, because each size class has a unique acoustic signature. In this way the presence of very large particles, in a size range identified as coarse material or 'rocks', can be clearly detected and quantified based on their acoustic signature.

The system consists of acoustic sensors externally mounted to the overflow pipe as shown in FIGS. 3a, 3b and 3c. Signals may be transmitted via a local amplifier to a processor mounted on the cyclone battery, which then transmits to a PC located in the control room. A graphical user interface shown in FIG. 3d provides real-time status for each cyclone, which includes: on-off state, three-state rock even severity (none, moderate, severe), and rock event level trending.

It has also been set forth that the present technique can be extended to identify an abnormally high fraction of particles larger than the separation size, but smaller than the coarse material or 'rock' size, as described above. The potential to monitor the amount of this oversize material in real-time could be highly useful in further hydrocyclone performance optimization, and thus increase overall mineral recovery in the concentrator plant, and reduce energy consumption in grinding.

Sonar-Based Flow Monitoring

As one skilled in the art would appreciate, SONAR array-based flow measurement technology was introduced into the mineral processing industry about five years ago, and has since demonstrated significant usefulness and value in many difficult and critical flow monitoring applications. This robust non-invasive technology has become the standard for many companies in certain applications.

For the purpose of understanding the present invention, presented below is a summary of some application experience, lessons learned, and best practices from installations world wide. Highlighted applications include: cyclone feed flow measurement, measuring aerated flows for mass balance correction, stratification and sanding detection in horizontal slurry lines, slurry pipeline flow monitoring and leak detection.

Also shown, will be how the basic volumetric flow rate, combined with the unique additional measurements of speed of sound, entrained air volume, can enable novel solutions to monitoring and control problems that are not possible with other flow technologies.

Recent product development work will be presented showing how the same fundamental sensor technology can be used to obtain robust, high quality acoustic signals which can be used to monitor and control key flow related process equipment in the beneficiation process, and improve process performance. Results of in-plant tests will be presented.

In general, since its introduction to the mining industry five years ago, sonar array-based technology has achieved rapid and widespread acceptance, achieving approximately 1,000 installations in over 150 mine sites in 20 countries. This has happened because using traditional flowmeter technology such as electromagnetic, ultrasonic Doppler, differential pressure, or Coriolis to obtain true flow measurement has proven to be a challenge for process control engineers because of many process influences. These influences include changing process fluid properties, calibration drift, pipe wall scale buildup, presence of magnetite, and the presence of entrained air. It is now possible to perform accurate flow measurements in the presence of these influences through the use of the latest generation of flow measurement technology based on the use of arrays of passive acoustic sensors. The present invention is described in relation to the basic operating principles presented herein, along with an understanding of some application examples from the first five years of commercial use and the lessons learned.

Basic Operating Principles

The basic operating principles are described in relation to FIGS. 13-19 below:

Volumetric Flow Measurement—Basic Operating Principle

Through the combination of an array of passive sensors and sonar array processing algorithms, the average axial velocities of a collection of vortices or density variations may be obtained. The sequence of events that occur to make this measurement possible is as follows, and illustrated in FIG. 13.

The passage of the turbulent eddies or density variations creates a small pressure change on the inside of the pipe wall This small pressure change results in a dynamic strain of the pipe wall itself (FIG. 13 exaggerates)

The mechanical dynamic strain signal is converted to an electrical signal through a passive sensor wrapped partially or fully around the pipe—no couplant gels or liquids are required This electrical signal is detected by each element of the array of sensors.

These sensors are spaced a precisely set distance from each other along the axial direction of the pipe.

The resulting electrical signal from each sensor element is interpreted as a characteristic signature of the frequency and phase components of the acoustic waves under the sensor.

An array processing algorithm combines the phase and frequency information of the characteristic signature from the group of sensor array elements to calculate the velocity of the characteristic signature as it propagates under the array of sensors.

Gas Volume Fraction Determination Based on Speed of Sound Measurement—Basic Operating Principles The array based technology may also be used to track acoustic waves travelling in the fluid. In most mineral processing plants there is an abundance of acoustic waves propagating within the process pipes. These acoustic waves are generated naturally from a variety of sources. These sources include pumps, the flow through pipe geometry changes and bubbles within the fluid that generate acoustic waves through their natural oscillations. These acoustic waves are low frequency (in the audible range), and travel in the pipe's axial direction, with wavelengths much longer than the entrained gas bubbles and the pipe diameter.

In multiphase fluids that consist of a gas mixed with a liquid or slurry, the acoustic velocity can be used to determine the amount of entrained gas (gas volume fraction) when the gas is in the form of bubbles that are well mixed within the liquid or slurry. Since the wavelengths of the acoustic waves are much larger than the bubble size, a complex interaction takes place that sets the acoustic velocity to be a strong function of the gas volume fraction. The speed of sound is proportional to the square root of the ratio of the compressibility and the density, both of which are heavily influenced by air content. An example of the resulting relationship is shown in FIG. 14. Error! Reference source not found. The particular values outlined by the curve in FIG. 14 are influenced by other factors, particularly pressure. Thus pressure at the location of the array based instrument must be measured or calculated. Once pressure is determined, the array based instrument is used to accurately measure the speed of sound, and the relationship between speed of sound and entrained air content is used to accurately quantify the amount of entrained air.

Operational Case Studies—Lessons Learned

Feed to Hydrocyclone Battery and Screen: Comparison of Array-Based Flowmeter and Electromagnetic Flowmeter to Pressure Readings At a minerals processing installation site, the array-based flowmeter was compared to an electromagnetic flowmeter for accuracy and noise performance. Both flowmeters were installed on a vertical section of a 300 mm polyethylene pipe as illustrated in the right side of FIG. 15. The flow passed through both flowmeters and then up into a distribution box that was instrumented with a pressure transducer. The readings from the two flowmeters, the pressure transducer, a nuclear density gauge, a sump level sensor, and pump speed were recorded at five second intervals. During the data acquisition period, the density and sump level were fairly constant, thus the outputs of the flowmeters were compared only to the pressure and pump speed. Since the flow discharged from the distribution box through a series of valves to atmospheric pressure, the readings from the pressure transducer were used as a form of differential pressure flow measurement. The pressure is a function of the number of valves open and their position, the density of the slurry, and the square of the velocity. With constant valve conditions and density, the pressure is assumed to vary only as a function of the square of the velocity.

Likewise the velocity reported by each flowmeter should vary as a function of the square root of the pressure as illustrated by a comparison of the array-based flowmeter readings versus the pressure readings as shown in the right side (FIG. 16b) of FIG. 16. Due to the spread in the readings from the electromagnetic flowmeter, this is difficult to see by using the electromagnetic flowmeter readings as seen on the left side (FIG. 16a) of FIG. 16. After application of heavy filtering to the electromagnetic flowmeter reading, an overall trend relative to the readings from the pressure transducer and array-based flowmeters can be seen in FIG. 17. The resulting erroneous dips in the electromagnetic flowmeter readings cannot be explained by magnetic material passing through the flowmeter or material striking the electrodes. In contrast, the array-based flowmeter exhibits excellent agreement with the pressure reading.

Measuring Aerated Flows for Mass Balance Improvement

The accurate measurement of the percentage of pipe volume occupied by gas bubbles in a liquid also known as gas void fraction can lead to a true volumetric flow measurement, a corrected density measurement and a true solids mass flow rate calculation. Before the introduction of array-based technology, it was not possible to perform this measurement from the outside of the pipe in slurry flows.

Volumetric Flow Correction for Entrained Air

Quite a few steps in a process require the accurate measurement of volumetric flow rates. Examples include cyclone feed rates for control of separation and sharpness of cut, and flotation feed rates for control of flotation residence times. In many cases, both expected and unexpected, gas in the form of entrained air bubbles can enter into a pipe conveyed slurry stream. This entrained air occupies space within the pipe thus leading to an overall volumetric flow rate that is the sum of both the gas volumetric flow rate and the slurry flow rate which is the combined solids and liquid volumetric flows. Assuming that the air bubbles and the slurry travel at the same velocity, which is a valid assumption for horizontal flows, and for vertical flows in the case of small bubbles or high slurry velocities, the total volumetric flow rate can be expressed in the form of the phase fraction of the air or gas component $Q_T = Q_G + Q_{SL}$ (Equation 1), where $Q_T$ is the total volumetric flow rate; $Q_G$ is the gas volumetric flow rate; and $Q_{SL}$ is the slurry volumetric flow rate QT=QG+QSL (Equation 1 which can be rewritten as: $Q_T = \phi_G Q_T + Q_{SL}$ (Equation 2)), where $\phi_G$ is the phase fraction of the gas component, also known as the gas void fraction or GVF. Using Equation 2, one can solve for $Q_{SL}$ to obtain:

$$Q_{SL} = Q_T - \phi_G Q_T = (1 - \phi_G) Q_T \quad \text{(Equation 3)}.$$

Thus the correction uses a simple linear equation.

Slurry Density Correction for Entrained Air

Measurement of slurry density is used for both control and monitoring purposes including cyclone control to maintain the separation and sharpness of the cut, in dense medium separation to control the separation density, and in thickener underflows to control the pull rate. As with volumetric flow, entrained air bubbles will cause an error in the required measurement when this measurement is performed by commonly employed nuclear density gauges or less frequently by Coriolis meters. The particular impact of entrained air bubbles on the mixture is as follows:

$$\rho_m = \phi_G \rho_G + \phi_{SL} \rho_{SL}, \quad \text{(Equation 4)},$$

where as before $\phi_G$ is the volumetric phase fraction of the gas; $\rho_G$ is the density of the gas component; $\phi_{SL}$ is the volumetric phase fraction of the slurry; and $\rho_{SL}$ is the density the slurry without air.

Now since by definition $\phi_G + \phi_{SL} = 1$, one obtains $$\phi_{SL} = 1 - \phi_G \quad \text{(Equation 5)}$$

Combining equations 4 and 5, one obtains:

$$\rho_m = \phi_G + (1 - \phi_G) \rho_{SL} \quad \text{(Eqn 6)}$$

This in turn can be rewritten as:

$$\rho_m = \rho_{SL} + (\rho_G - \rho_{SL}) \phi_G \quad \text{(Eqn 7)}.$$

Now since $\rho_G \ll \rho_{SL}$ this can be simplified as:

$$\rho_m = \rho_{SL} - \rho_{SL} \phi_G \text{ or } \rho_m = (1 - \phi_G) \rho_{SL} \quad \text{(Eqn 8)}.$$

In terms of this can be expressed as $$\rho_{SL} = \rho_m / (1 - \phi_G) \quad \text{(Eqn 9)}$$

Solids Weight Fraction (Cw) Correction for Entrained Air

It is known to use solids weight fraction when referring to solids content in the slurry and when calculating solids mass flow rates such as ton/hr or kg/hr. Solids weight fraction can be measured directly via a sampling and drying technique but real time determination of solids weight fraction is typically performed by using the density measurement from a nuclear density gauge and using the density of the dry solids to calculate the solids weight fraction. This calculation can be done by a PLC, other control systems or within the nuclear density gauge itself. This calculation is based on a formula similar to the following:

$$C_W = \frac{[\rho_{SL} - \rho_L]}{[\rho_S - \rho_L]} \frac{\rho_S}{\rho_{SL}} \quad \text{(Eqn 10)}$$

where $\rho_{SL}$ is the slurry density (if there is no entrained air then this is the density reported from the density gauge); $\rho_L$ is the liquid density (typically water density); and $\rho_S$ is the dry solids density Now if there are air bubbles present then the density reported by the density meter will not be the actual slurry (solids and liquid portion) density, and $C_W$ will be in error. If there are air bubbles present then the density gauge will report $\rho_m$ which is the density of the air, liquid and solids mixture. To obtain the correct $C_W$ equation 9 is combined with equation 10 to obtain:

$$C_{W,Corrected} = \frac{[\rho_m / (1 - \phi_G) - \rho_L]}{[\rho_S - \rho_L]} \frac{\rho_S}{\rho_m / (1 - \phi_G)} \quad \text{(Eqn 11)}$$

where $\rho_m$ is the density reported by the density gauge and $\phi_G$ is the volume phase fraction of the air bubbles Solids Mass Flowrate Correction When performing metallurgical accounting, mass balancing, dosing of chemicals such as flocculants, it is important to know the solids mass flow rate such tons/h or kg/h. The solids mass flow rate is calculated from measurements of mixture density and volumetric flow rate, along with the results from calculating solids weight fraction ($C_W$).

$$\dot{M}_S = C_W \rho_{SL} Q_{SL} \qquad \text{(Eqn 12)}$$

where $\rho_{SL}$ is the slurry density and $Q_{SL}$ is the slurry volumetric flow rate. If air bubbles are present then the equation should take the gas void fraction into account, resulting in the equation:

$$\dot{M}_{S,Corrected} = C_{W,Corrected} \frac{\rho_m}{1-\phi_G} Q_T (1-\varphi_G) = C_{W,Corrected} \rho_m Q_T$$

Now the gas void fraction does cancel out in part of the equation as shown in equation 13, thus leaving an expression in which the error introduced by the air bubbles is captured within the calculated variable $C_{W,Corrected}$. The full expression is then:

$$\dot{M}_{S,Corrected} = \frac{[\rho_m/(1-\phi_G)-\rho_L]}{[\rho_S-\rho_L]} \frac{\rho_S}{\rho_m/(1-\phi_G)} \rho_m Q_T = \frac{[\rho_m-\rho_L(1-\phi_G)]}{[\rho_S-\rho_L]} \frac{\rho_S}{\rho_m} \rho_m Q_T$$

If the entrained air is not taken into account we have this expression:

$$\dot{M}_{S,Uncorrected} = C_{W,Uncorrected} \rho_m Q_T = \frac{[\rho_m-\rho_L]}{[\rho_S-\rho_L]} \frac{\rho_S}{\rho_m} \rho_m Q_T$$

The relative error can be taken by taking the ratio between the uncorrected solids mass flow rate and the corrected solids mass flow rate, along with subtracting one from the ratio.

$$\text{Error} = \frac{\dot{M}_{S,Uncorrected}}{\dot{M}_{S,Corrected}} - 1 = \frac{\frac{[\rho_m-\rho_L]}{[\rho_S-\rho_L]} \frac{\rho_S}{\rho_m} \rho_m Q_T}{\frac{[\rho_m/(1-\phi_G)-\rho_L]}{[\rho_S-\rho_L]} \frac{\rho_S}{\rho_m/(1-\phi_G)} \rho_m Q_T} - 1$$

This can be easily simplified to the following form $$\text{Error} = \frac{[\rho_m-\rho_L]}{[\rho_m-\rho_L(1-\phi_G)]} - 1 =$$

$$\frac{[\rho_m-\rho_L]-[\rho_m-\rho_L(1-\phi_G)]}{[\rho_m-\rho_L(1-\phi_G)]} = \frac{-\rho_L \phi_G}{\rho_m-\rho_L(1-\phi_G)} = \frac{-\phi_G}{\frac{\rho_m}{\rho_L}-1+\phi_G}$$

Slurry Pipeline Stratification and Sanding Detection with Three Flowmeters

A serious problem in slurry pipelines is the occurrence of highly stratified flow conditions which can quickly lead to solids deposition and the forming of moving or stationary solids beds in the pipe. Early detection of such conditions in real time has suffered from instrumentation limitations. However three sonar flowmeters mounted at strategic locations can provide such information.

The sonar flowmeter has been designed to measure multiphase flows such as liquid-solid slurries, and therefore is insensitive to large variations in flow profile caused by stratification of solids. However when stratification becomes severe, and a large fraction of solids are moving slowly near the bottom of the pipe and approaching a sanding condition, the effective pipe cross section area for calculating volumetric flow is reduced, the velocity in the upper portion of the pipe increases, and the sonar meter reports a higher flow rate. Actually, since the sonar meter is fundamentally a velocity meter, it is measuring the velocity first and then calculating a volumetric flow based on an area that is no longer correct. The key to using this effect is to have a reference flow rate to compare against that is not affected by the stratification condition. This can be accomplished by locating two sonar flowmeters at positions where the slurry is known to be well mixed and thus not stratified, and one or more sonar meters at locations where slurry mixing is poor and stratification more likely. FIG. 18 shows such a generic pipe configuration, with sonar meters at well-mixed locations at km 0 and km 50. A third sonar meter—the stratification detector—is near km 49.9 has no up-stream feature that would cause mixing, and in fact is at the end of a multi-kilometer straight uphill section where high stratification is more expected due to gravity effects. FIG. 18 also shows all three meters tracking well at flow rates in the 7,000 m^3/h to 9,000 m^3/h range. However at approximately 21:00 hours on 29 Jul. 2010, the flow rate is reduced to 6,000 m^3/h, at which time the stratification detection sonar meter begins to increase while the other two meters continue to correlate well, indicating a highly stratified flow condition exists at the detection meter. It can also be seen that the density meter begins to trend lower at the same time that the stratification detection sonar flowmeter meter trends higher, indicating that solids are accumulating (or being 'held up') in the uphill section of the pipeline due to stratification, thus causing the density meter at the well-mixed location to report the lower density.

Slurry Pipeline Leak Detection

Concern over the consequences of slurry pipeline leaks has become increasingly important, as society has become highly intolerant of owners and operators using unsafe practices, and equipment that is not the best technology economically available. Commercial slurry leak detection systems typically rely on two basic methods:

Mass Balance Leak Detection. Commonly known by this name, in practice it is based on a volume balance. The volume that passes one point should pass through another point, within a certain tolerance; if not, then there is a leak. From an implementation standpoint, the system compares the volumetric flow rates at different locations along the pipeline. The ability to detect smaller leaks requires higher accuracy from the flowmeters used to provide the volumetric flow rate measurements. The ability to determine the leak location along the pipeline is defined by the distance between adjacent pairs of flowmeters.

Pressure Wave Leak Detection. When a sudden leak occurs, a pressure wave is generated that propagates upstream and downstream of the leak location. This wave is detectable with standard pressure sensor instrumentation and data acquisition technologies. Since the wave moves at a known speed (the speed of sound in the fluid), both the existence of the sudden leak and the location can be estimated.

It is important to understand the differences between the two methods and the resulting capabilities and limitations of each. The pressure wave method requires a sudden leak to produce a pressure wave of clearly detectable amplitude. However many leaks start slowly and gradually increase in flow rate, thus never producing a clearly detectable pressure wave, making the leak undetectable. The volume balance method can detect small flow rate changes and slow trends in flow rate, and thus can detect small leaks that are not detectable by the presser wave method. Clearly, a good slurry leak detection system should use both techniques.

However measuring slurry flow rate with accuracy, repeatability and reliability has always been challenging, and too frequently unattainable with commonly used invasive electromagnetic flowmeters. For these devices, highly abrasive flows cause constant wear to flowmeter parts exposed to the flow, and the presence of even small amounts of magnetic material can produce large errors. The sonar meter overcomes these limitations.

Figure 19:
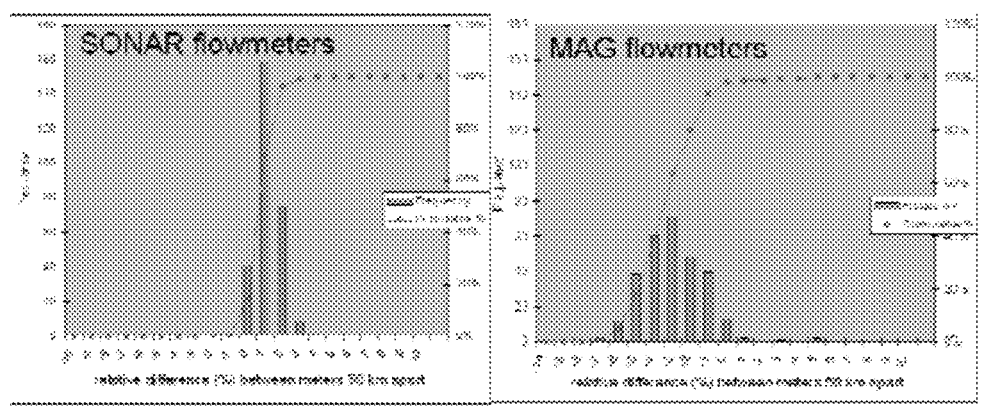
FIG. 19 shows a basic operating principle related to feed to a hydrocyclone battery and screen related to a difference in flowrate in the form of graphs of frequency versus a relative difference (%) between meters 50 km apart, one for SONAR flowmeters and another for MAG flowmeters, the understanding of which may be used for implementing some embodiments of the present invention.

FIG. 19 shows a comparison between two electromagnetic and two sonar flowmeters on a 50 km tailings line. A sonar and mag meter are located at each end of the line. The histograms show that both the absolute difference and the average deviation between similar meters is less for the sonar meter pair.

Applications Re Other Industrial Processes

By way of example, the present invention is described in relation to, and part of, a mineral extraction processing system for extracting minerals from ore. However, the scope of the invention is intended to include other types or kinds of industrial processes either now known or later developed in the future, including any mineral process, such as those related to processing substances or compounds that result from inorganic processes of nature and/or that are mined from the ground, as well as including either other extraction processing systems or other industrial processes, where the sorting, or classification, of product by size is critical to overall industrial process performance.

The Scope of the Invention

While the invention has been described with reference to an exemplary embodiment, it will be understood by those skilled in the art that various changes may be made and equivalents may be substituted for elements thereof without departing from the scope of the invention. In addition, may modifications may be made to adapt a particular situation or material to the teachings of the invention without departing from the essential scope thereof. Therefore, it is intended that the invention not be limited to the particular embodiment(s) disclosed herein as the best mode contemplated for carrying out this invention.

What is claimed is:

1. Apparatus, including a non-invasive acoustic-based passive monitoring system, comprising:
cyclones configured in parallel to form a cyclone battery in a mineral extraction process in order to process a slurry, each cyclone having an overflow pipe for providing some portion of the slurry flowing in the cyclone battery;
sensors, each sensor configured to mount on a respective overflow pipe of a respective cyclone, to respond to sound propagating through the slurry flowing in the respective overflow pipe of the respective cyclone, and to provide a respective signal containing information about the sound propagating through the slurry flowing in the respective overflow pipe of the respective cyclone; and
a signal processor configured to respond to respective signals from the sensors and determine corresponding signals containing information to control the individual cyclones that are flowing at any given time by monitoring and tracking a respective individual cyclone flow performance of each of the individual cyclones, based on the respective signals received;
wherein the signal processor is configured to:
respond to signaling containing information about a battery flow rate, battery pressure, feed density, and cyclone status as indicated by individual gate valve positions of respective cyclones, the cyclone status the number individual cyclones in operation,
decompose average flow per cyclone versus density scaled pressure by actual cyclone combinations open to flow, and
determine a flow performance of the actual cyclone combinations; and
wherein the signal processor is configured to determine a cyclone performance curve based at least on an equation:

$$\log(q) = a \times \log\left(\frac{p}{\rho}\right) + b, \tag{1}$$

where q is a cyclone flow rate, p is a battery pressure, ρ is a slurry density, and a is the slope of the equation, and b is an intercept of the equation.

2. The apparatus according to claim 1, wherein the signal processor is configured to determine the individual cyclone flow performance based at least partly on a size distribution of an overflow stream provided from an overflow pipe of a cyclone in the cyclone battery.

3. The apparatus according to claim 1, wherein at least one sensor is a sonar-based clamp-around flow meter.

4. The apparatus according to claim 3, wherein the sonar-based clamp-around flow meter is configured to respond to a strain imparted by the slurry made up of water and fine particles flowing in the respective overflow pipe of the respective cyclone, and provide the respective signal containing information about sound propagating through the slurry flowing in the respective overflow pipe of the respective cyclone.

5. The apparatus according to claim 4, wherein the respective signal is an amplitude-based time domain signal and has a frequency spectrum signature, and the at least one signal processor module is configured to respond to the signals and determine the individual cyclone flow performance of each cyclone and take real time control action to optimize a cyclone battery flow performance of the cyclone battery.

6. The apparatus according to claim 5, wherein the signal processor is configured to perform some combination of the following:
detect course material, rocks, in the overflow pipe; or
detect oversize material in an overflow stream; or detect a flowing and/or non-flowing cyclone condition of a cyclone; or based on a detected flow performance of individual cyclones, employ a control strategy to maximize the cyclone battery availability and reduce an amount of large particle discharge sent to a flotation stage.

7. The apparatus according to claim 6, wherein the signal processor is configured to detect course material, rocks, including particles whose size are greater than 0.1" in diameter, in the overflow pipe by processing the amplitude-based time domain signal and determining when a rock impacts the wall of the pipe, including by first taking the acceleration of the amplitude-based time domain signal and then processing that with a peak detection algorithm.

8. The apparatus according to claim 6, wherein the signal processor is configured to detect oversize material in the respective overflow pipe by feeding a neural net based algorithm a measured real time frequency spectrum, where the neural net based algorithm has been trained to recognize one spectrum that represents a size distribution that is representative of a design set point and another spectrum that does not.

9. The apparatus according to claim 6, wherein the signal processor is configured to detect the flowing and/or non-flowing cyclone condition, where a feed to the respective cyclone is controlled with a gate valve, by detecting that there is not flow to the respective cyclone when the gate valve is closed, and by detecting that a feed flow enters the respective cyclone when the gate valve is open, where the neural net based algorithm has been trained to recognize the spectrum that represents both a flowing condition and a non-flowing condition.

10. The apparatus according to claim 6, wherein the signal processor is configured to employ a control strategy to maximize the cyclone battery availability and reduce the amount of large particle discharge sent to flotation, where cyclone battery feed flow, feed density, and pressure are used to control a number of cyclones that are flowing at any given time, using an open loop process, by monitoring the individual cyclone flow performance of individual cyclones and doing one or more of the following:

turning off cyclones that are performing poorly; or optimizing the number of cyclones that are flowing for a given plant operating condition; or developing a predicative maintenance schedule by trending the individual cyclone flow performance over time.

11. The apparatus according to claim 1, wherein each sensor is configured to respond to a strain imparted by the slurry made up of water and fine particles flowing in the respective overflow pipe of the respective cyclone, and provide the respective signal containing information about sound propagating through the slurry flowing in the respective overflow pipe of the respective cyclone.

12. The apparatus according to claim 11, wherein the signal processor is configured to selectively open and close one or more of the cyclones based at least partly on the information contained in the respective signals.

13. The apparatus according to claim 1, wherein the signal processor is configured to provide the corresponding signals as an output signal containing information that identifies the on-off status of individual cyclones, a qualitative alarm that identifies a severity of rock events detected, and a quantitative measure of the number rocks detected vs time.

14. The apparatus according to claim 1, wherein the signal processor is configured to provide the corresponding signals as an output signal containing information to take corrective action, including shutting off an offending cyclone, or adjusting other operating parameters that include a changing flow rate, feed density, or battery pressure based at least partly on an optimized optimize cyclone flow performance by identifying poorly performing cyclones, or some combination thereof.

15. The apparatus according to claim 1, wherein the signal processor provides the corresponding signals as an output signal containing information to allow an operator to optimize cyclone flow performance, including real-time cyclone information for displaying on a control room display.

16. The apparatus according to claim 1, wherein the signal processor provides the corresponding signals as an output signal containing information to control the operation of the cyclones in the cyclone battery to optimize cyclone flow performance.

17. The apparatus according to claim 1, wherein signal processor is configured to determine the presence of particles in various general size classes based on each size class having a unique acoustic signature.

18. The apparatus according to claim 17, wherein the signal processor is configured to monitor an amount of oversize material in real-time to further cyclone flow performance optimization, increase overall mineral recovery in a concentrator plant, and/or reduce energy consumption in a grinding process.

19. Apparatus, including a non-invasive acoustic-based passive monitoring system, comprising:

cyclones configured in parallel to form a cyclone battery in order to process a slurry, each cyclone having parts for processing some portion of the slurry flowing in the cyclone battery;

sensors, each sensor configured to mount on a respective part of a respective cyclone, to respond to sound propagating through the slurry flowing in the respective part of the respective cyclone, and to provide a respective signal containing information about the sound propagating through the slurry flowing in the respective part of the respective cyclone; and a signal processor configured to respond to respective signals from the sensors and determine corresponding signaling containing information to control the individual cyclones that are flowing at any given time by monitoring and tracking a respective individual cyclone flow performance of each of the individual cyclones, based on the respective signals received;

wherein the at least one signal processor is configured to:
respond to signaling containing information about a battery flow rate, battery pressure, feed density, and a cyclone status as indicated by individual gate valve positions of respective cyclones, the cyclone status including a number of the individual cyclones in operation, decompose average flow per cyclone versus density scaled pressure by actual cyclone combinations open to flow, and determine a flow performance of the actual cyclone combinations; and wherein the at least one signal processor is configured to determine a cyclone performance curve based at least on an equation:

$$\log(q) = a \times \log\left(\frac{p}{\rho}\right) + b, \tag{1}$$

where q is a cyclone flow rate, p is a battery pressure, $\rho$ is a slurry density, and a is a slope of the equation, and b is an intercept of the equation.

20. The apparatus according to claim 19, wherein the parts further comprise an inlet portion, a cylindrical section, a conical base section, an overflow pipe, or an underflow outlet, or a combination thereof.

21. The apparatus according to claim 19, wherein said each sensor is mounted on the top of the respective part, mounted on the bottom of the respective part, mounted on the top and bottom of the respective part, mounted partially or substantially around the respective part, mounted along the length of the respective part, or some combination thereof.

* * * * *